(12) United States Patent
Tebbe et al.

(10) Patent No.: US 10,588,663 B2
(45) Date of Patent: Mar. 17, 2020

(54) DILATOR

(71) Applicant: VertiFlex, Inc., Carlsbad, CA (US)

(72) Inventors: Shawn Tebbe, Leixlip (IE); Moti Altarac, Irvine, CA (US); Yang Cheng, Foothill Ranch, CA (US)

(73) Assignee: VERTIFLEX, INC., Carlsbad, CA (US)

( * ) Notice: Subject to any disclaimer, the term of this patent is extended or adjusted under 35 U.S.C. 154(b) by 0 days.

(21) Appl. No.: 15/431,255

(22) Filed: Feb. 13, 2017

(65) Prior Publication Data

US 2017/0245883 A1    Aug. 31, 2017

Related U.S. Application Data

(63) Continuation of application No. 14/496,820, filed on Sep. 25, 2014, now Pat. No. 9,566,086, which is a
(Continued)

(51) Int. Cl.
*A61B 17/02*    (2006.01)
*A61B 17/34*    (2006.01)
(Continued)

(52) U.S. Cl.
CPC ........ *A61B 17/3468* (2013.01); *A61B 17/025* (2013.01); *A61B 17/3421* (2013.01);
(Continued)

(58) Field of Classification Search
CPC .............. A61B 17/025; A61B 17/3421; A61B 17/32093; A61B 17/7062; A61B 17/256; A61B 17/06085; A61B 17/3454
See application file for complete search history.

(56) References Cited

U.S. PATENT DOCUMENTS 2,248,054 A    7/1941 Becker
2,677,369 A    5/1954 Knowles
(Continued)

FOREIGN PATENT DOCUMENTS

CA        268461 A     2/1927
CN     2794456 Y     7/2006
(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
(Continued)

*Primary Examiner* — Christopher D. Prone
(74) *Attorney, Agent, or Firm* — Lowe Graham Jones PLLC; Bruce E. Black

(57) ABSTRACT

A dilator that facilitates implantation of an interspinous spacer is provided. The dilator includes a proximal portion and a tapered distal portion interconnected by an elongated body portion. The tapered distal portion is ideally suited for splitting ligamentous tissue for creating a posterior midline pathway through the supraspinous ligament as well as for distracting the adjacent spinous processes. Two oppositely located and longitudinally extending channels or grooves are formed in the outer surface of the dilator for stabilizing the dilator with respect to the spinous processes. An accompanying cannula together with the dilator form a system for the distraction of the adjacent spinous processes, stabilization of the spinous processes with respect to the system and creation of a working channel for the implantation of an interspinous spacer.

24 Claims, 29 Drawing Sheets

Related U.S. Application Data continuation of application No. 12/358,010, filed on Jan. 22, 2009, now Pat. No. 8,845,726, which is a continuation-in-part of application No. 11/582,874, filed on Oct. 18, 2006, now Pat. No. 8,128,662.

(60) Provisional application No. 61/062,448, filed on Jan. 23, 2008.

(51) Int. Cl.
| | | |
|---|---|---|
| A61M 29/00 | (2006.01) | |
| A61B 17/3209 | (2006.01) | |
| A61B 17/3211 | (2006.01) | |
| A61B 17/70 | (2006.01) | |
| A61B 17/32 | (2006.01) | |

(52) U.S. Cl.
CPC .......... *A61M 29/00* (2013.01); *A61B 17/3211* (2013.01); *A61B 17/32093* (2013.01); *A61B 17/7062* (2013.01); *A61B 2017/0256* (2013.01); *A61B 2017/320044* (2013.01); *A61B 2017/346* (2013.01); *A61B 2017/3454* (2013.01)

(56) References Cited

U.S. PATENT DOCUMENTS

| | | | |
|---|---|---|---|
| 3,242,120 | A | 3/1966 | Steuber |
| 3,486,505 | A | 12/1969 | Morrison |
| 3,648,691 | A | 3/1972 | Lumb et al. |
| 3,780,733 | A | 12/1973 | Martinez-Manzor |
| 3,986,383 | A | 10/1976 | Petteys |
| 4,545,374 | A | 10/1985 | Jacobson |
| 4,632,101 | A | 12/1986 | Freedland |
| 4,685,447 | A | 8/1987 | Iversen et al. |
| 4,799,484 | A | 1/1989 | Smith et al. |
| 4,863,476 | A | 9/1989 | Shepperd |
| 4,895,564 | A | 1/1990 | Farrell |
| 4,986,831 | A | 1/1991 | King et al. |
| 5,011,484 | A | 4/1991 | Breard et al. |
| 5,015,247 | A | 5/1991 | Michelson |
| 5,019,081 | A | 5/1991 | Watanabe |
| 5,040,542 | A | 8/1991 | Gray |
| 5,059,193 | A | 10/1991 | Kuslich |
| 5,092,866 | A | 3/1992 | Breard et al. |
| 5,178,628 | A | 1/1993 | Otsuka et al. |
| 5,180,393 | A | 1/1993 | Commarmond et al. |
| 5,182,281 | A | 1/1993 | Frigola-Constansa et al. |
| 5,188,281 | A | 2/1993 | Fujiwara et al. |
| 5,192,281 | A | 3/1993 | de la Caffiniere |
| 5,195,526 | A | 3/1993 | Michelson |
| 5,298,253 | A | 3/1994 | LeFiles et al. |
| 5,368,594 | A | 11/1994 | Martin et al. |
| 5,390,683 | A | 2/1995 | Pisharodi |
| 5,415,661 | A | 5/1995 | Holmes |
| 5,456,722 | A | 10/1995 | McLeod et al. |
| 5,462,738 | A | 10/1995 | LeFiles et al. |
| 5,472,452 | A | 12/1995 | Trott |
| 5,484,437 | A | 1/1996 | Michelson |
| 5,487,739 | A | 1/1996 | Aebischer et al. |
| 5,489,308 | A | 2/1996 | Kuslich et al. |
| 5,496,318 | A | 3/1996 | Howland et al. |
| 5,531,748 | A | 7/1996 | de la Caffiniere et al. |
| 5,549,679 | A | 8/1996 | Kuslich |
| 5,571,189 | A | 11/1996 | Kuslich |
| 5,591,165 | A | 1/1997 | Jackson |
| 5,609,634 | A | 3/1997 | Voydeville et al. |
| 5,609,636 | A | 3/1997 | Kohrs et al. |
| 5,645,599 | A | 7/1997 | Samani et al. |
| 5,654,599 | A | 8/1997 | Casper |
| 5,658,337 | A | 8/1997 | Kohrs et al. |
| 5,674,295 | A | 10/1997 | Ray et al. |
| 5,700,264 | A | 12/1997 | Zucherman et al. |
| 5,725,582 | A | 3/1998 | Bevan et al. |
| 5,741,253 | A | 4/1998 | Michelson |
| 5,746,720 | A | 5/1998 | Stouder, Jr. |
| 5,762,629 | A | 6/1998 | Kambin |
| 5,836,948 | A | 11/1998 | Zucherman et al. |
| 5,860,977 | A | 1/1999 | Zucherman et al. |
| 5,863,948 | A | 1/1999 | Epstein et al. |
| 5,876,404 | A | 3/1999 | Zucherman et al. |
| RE36,211 | E | 5/1999 | Nonomura et al. |
| 5,904,636 | A | 5/1999 | Chen et al. |
| 5,904,686 | A | 5/1999 | Zucherman et al. |
| 5,928,207 | A | 7/1999 | Pisano et al. |
| 5,948,017 | A | 9/1999 | Taheri |
| 5,972,015 | A | 10/1999 | Scribner et al. |
| 6,039,761 | A | 3/2000 | Li et al. |
| 6,045,552 | A | 4/2000 | Zucherman et al. |
| 6,048,342 | A | 4/2000 | Zucherman et al. |
| 6,048,345 | A | 4/2000 | Berke et al. |
| 6,066,154 | A | 5/2000 | Reiley et al. |
| 6,068,630 | A | 5/2000 | Zucherman et al. |
| 6,074,390 | A | 6/2000 | Zucherman et al. |
| 6,080,155 | A | 6/2000 | Michelson |
| 6,080,157 | A | 6/2000 | Cathro et al. |
| 6,090,112 | A | 7/2000 | Zucherman et al. |
| 6,096,038 | A | 8/2000 | Michelson |
| 6,102,928 | A | 8/2000 | Bonutti |
| D433,193 | S | 10/2000 | Gaw et al. |
| 6,132,464 | A | 10/2000 | Martin et al. |
| 6,149,642 | A | 11/2000 | Gerhart et al. |
| 6,149,652 | A | 11/2000 | Zucherman et al. |
| 6,152,926 | A | 11/2000 | Zucherman et al. |
| 6,156,038 | A | 12/2000 | Zucherman et al. |
| 6,159,215 | A | 12/2000 | Urbahns et al. |
| 6,179,873 | B1 | 1/2001 | Zientek |
| 6,183,471 | B1 | 2/2001 | Zucherman et al. |
| 6,190,387 | B1 | 2/2001 | Zucherman et al. |
| 6,225,048 | B1 | 5/2001 | Soderberg-Naucler et al. |
| 6,235,030 | B1 | 5/2001 | Zucherman et al. |
| 6,238,397 | B1 | 5/2001 | Zucherman et al. |
| 6,264,651 | B1 | 7/2001 | Underwood et al. |
| 6,264,656 | B1 | 7/2001 | Michelson |
| 6,267,763 | B1 * | 7/2001 | Castro .................. A61B 17/025 606/100 |
| 6,267,765 | B1 | 7/2001 | Taylor et al. |
| 6,270,498 | B1 | 8/2001 | Michelson |
| 6,280,444 | B1 | 8/2001 | Zucherman et al. |
| 6,312,431 | B1 | 11/2001 | Asfora |
| 6,328,730 | B1 | 12/2001 | Harkrider, Jr. |
| 6,332,882 | B1 | 12/2001 | Zucherman et al. |
| 6,332,883 | B1 | 12/2001 | Zucherman et al. |
| 6,336,930 | B1 | 1/2002 | Stalcup et al. |
| 6,348,053 | B1 | 2/2002 | Cachia |
| 6,364,883 | B1 | 4/2002 | Santilli |
| 6,371,989 | B1 | 4/2002 | Chauvin et al. |
| 6,375,682 | B1 | 4/2002 | Fleischmann et al. |
| 6,379,355 | B1 | 4/2002 | Zucherman et al. |
| 6,387,130 | B1 | 5/2002 | Stone et al. |
| 6,395,032 | B1 | 5/2002 | Gauchet et al. |
| 6,402,740 | B1 | 6/2002 | Ellis et al. |
| 6,402,750 | B1 | 6/2002 | Atkinson et al. |
| 6,402,784 | B1 | 6/2002 | Wardlaw et al. |
| 6,413,228 | B1 | 7/2002 | Hung et al. |
| 6,419,676 | B1 | 7/2002 | Zucherman et al. |
| 6,419,677 | B2 | 7/2002 | Zucherman et al. |
| 6,440,169 | B1 | 8/2002 | Elberg et al. |
| 6,443,988 | B2 | 9/2002 | Felt et al. |
| 6,447,547 | B1 | 9/2002 | Michelson |
| 6,451,019 | B1 | 9/2002 | Zucherman et al. |
| 6,451,020 | B1 | 9/2002 | Zucherman et al. |
| 6,464,682 | B1 | 10/2002 | Snoke |
| 6,471,976 | B1 | 10/2002 | Taylor et al. |
| 6,478,796 | B2 | 11/2002 | Zucherman et al. |
| 6,478,822 | B1 | 11/2002 | Leroux et al. |
| 6,500,178 | B2 | 12/2002 | Zucherman et al. |
| 6,514,256 | B2 | 2/2003 | Zucherman et al. |
| 6,530,925 | B2 | 3/2003 | Boudard et al. |
| 6,558,333 | B2 | 5/2003 | Gilboa et al. |
| 6,565,570 | B2 | 5/2003 | Sterett et al. |
| 6,572,617 | B1 | 6/2003 | Senegas et al. |
| 6,575,981 | B1 | 6/2003 | Boyd et al. |

(56) References Cited

U.S. PATENT DOCUMENTS

| | | |
|---|---|---|
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,616,673 B1 | 9/2003 | Stone et al. |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |

(56) References Cited

U.S. PATENT DOCUMENTS

| | | |
|---|---|---|
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 9,532,812 B2 | 1/2017 | Altarac et al. |
| 9,572,603 B2 | 2/2017 | Altarac et al. |
| 9,675,303 B2 | 6/2017 | Choi et al. |
| 9,861,398 B2 | 1/2018 | Altarac et al. |
| 2001/0031965 A1 | 10/2001 | Zucherman et al. |
| 2002/0022856 A1 | 2/2002 | Johnson et al. |
| 2002/0042607 A1 | 4/2002 | Palmer et al. |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0122458 A1 | 6/2006 | Bleich |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |

(56) References Cited

U.S. PATENT DOCUMENTS

| | | |
|---|---|---|
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Cads et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2015/0150598 A1 | 6/2015 | Tebbe et al. |
| 2015/0150604 A1 | 6/2015 | Kim |
| 2015/0374415 A1 | 12/2015 | Kim |

(56) References Cited

U.S. PATENT DOCUMENTS

| | | | |
|---|---|---|---|
| 2016/0030092 A1 | 2/2016 | Altarac et al. |
| 2016/0066963 A1 | 3/2016 | Kim |
| 2016/0135853 A1 | 5/2016 | Altarac et al. |
| 2016/0248222 A1 | 8/2016 | Miyata |
| 2016/0317193 A1 | 11/2016 | Kim |
| 2017/0071588 A1 | 3/2017 | Choi et al. |
| 2017/0128110 A1 | 5/2017 | Altarac et al. |
| 2017/0156763 A1 | 6/2017 | Altarac et al. |
| 2017/0258501 A1 | 9/2017 | Altarac et al. |
| 2017/0273722 A1 | 9/2017 | Altarac et al. |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A1 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A1 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A1 | 3/2007 |
| WO | WO-07075375 A2 | 7/2007 |
| WO | WO-07075788 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |
| WO | WO-07127677 A1 | 11/2007 |
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).

Fast, Avital et al., "Surgical Treatment of Lumbar Spinal Stenosis in the Elderly," Arch Phys. Med Rehabil., Mar. 1985, pp. 149-151, vol. 66.

International Search Report and Written Opinion; Application No. PCT/US2009/031710; dated Sep. 1, 2009, 10 pages.

(56) References Cited

OTHER PUBLICATIONS

Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).

Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).

McCulloch, John A., Young, Paul H., "Essentials of Spinal Microsurgery," 1998, pp. 453-485. Lippincott-Raven Publishers, Philadelphia, PA (37 pages total).

Minns, R.J., et al., "Preliminary Design and Experimental Studies of a Noval Soft Implant for Correcting Sagittal Plane Instability in the Lumbar Spine," (1997) Spine, 22(16): 1819-1827.

Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.

Swan, Colby, "Preliminary Design and Experimental Studies of a Novel Soft Implant for Correcting Sogittal Plane Instability in the Lumbar Spine," Spine, 1997, 22(16), 1826-1827.

Tredway, Trent L. et al., "Minimally Invasive Transforaminal Lumbar Interbody Fusion (MI-TLIF) and Lateral Mass Fusion with the MetRx System," (14 pages total), 2005.

Vaccaro, Alexander J. et al., MasterCases Spine Surgery, 2001, pp. 100-107. Thieme Medical Publishers, Inc., NY. (10 pages total).

Vertos mild Devices Kit—PRT-00430-C—Instructions for Use (13 pages total); see http://vertosmed.com/docs/mildIFU_PRT-00430-C.pdf., 2012.

\* cited by examiner

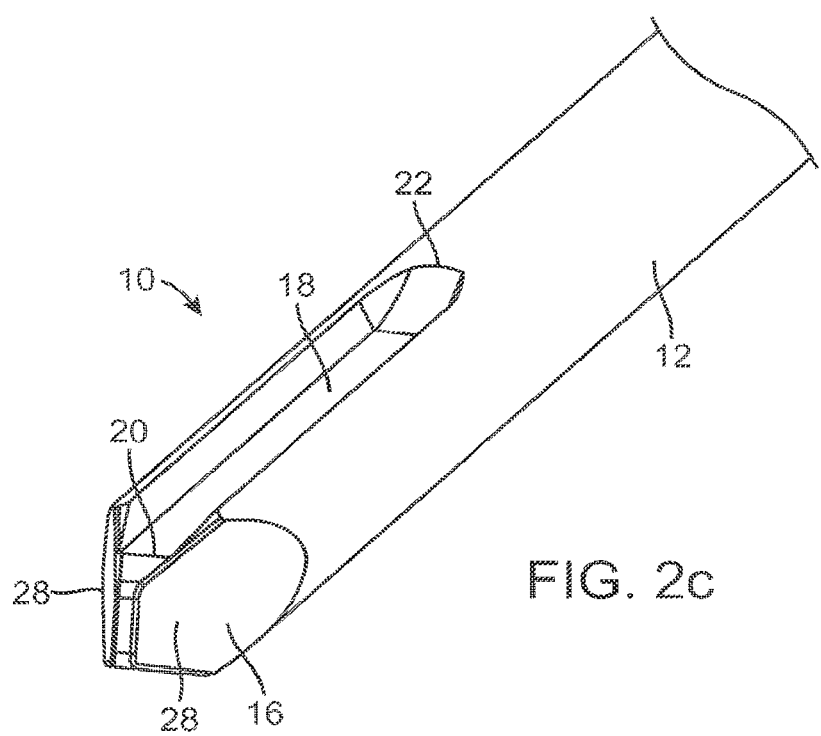

DILATOR

CROSS-REFERENCE TO RELATED APPLICATIONS

This application is a continuation of U.S. patent application Ser. No. 14/496,820 entitled "Dilator" filed on Sep. 25, 2014, now U.S. Pat. No. 9,566,086, which is a continuation of U.S. patent application Ser. No. 12/358,010 entitled "Dilator" filed on Jan. 22, 2009, now U.S. Pat. No. 8,845,726, which claims priority to and the benefit of and is a continuation-in-part of U.S. Provisional Patent Application No. 61/062,448 entitled "Dilator" filed on Jan. 23, 2008 which is incorporated herein by reference in its entirety. U.S. patent application Ser. No. 12/358,010 also claims priority to and is a continuation-in-part of U.S. patent application Ser. No. 11/582,874, now U.S. Pat. No. 8,128,662, entitled "Minimally invasive tooling for delivery of interspinous spacer" filed on Oct. 18, 2006 which is incorporated herein by reference in its entirety. Each of the above applications is incorporated by reference in its entirety.

BACKGROUND

A variety of retractors and dilation systems have been used to provide a traditional "open" or "mini-open" approach to the posterior spine, as well as for providing the more modern "minimally invasive" and "percutaneous" access to the spine. The "open" or "mini-open" approaches to the spine typically require larger incisions. These larger incisions readily provide visual and instrument access to the surgical site; however, larger incisions generally result in greater damage to muscle tissue, blood loss, long healing times accompanied by prolonged pain and significant scarring.

The development of minimally invasive, percutaneous procedures has provided a major improvement in reducing recovery time and post operative-pain. In minimally invasive, percutaneous techniques patient trauma is minimized by creating a relatively smaller incision, followed by the introduction of a series of successfully larger dilators installed in sequence to dilate the soft tissues and increase the effective size of the incision. In some cases, a guide wire is used to first access the surgical site and then cannulated dilators are installed over the wire. Following installation of the largest dilator deemed necessary, a cannula or retractor is advanced over the largest dilator for providing a working channel from the skin of the patient to the working space adjacent to the spine. Surgery is performed or an implant is inserted through a surgical port or cannula inserted into the dilated incision.

Instead of cutting a larger opening, sequential dilation splits the surrounding tissue to create a larger opening. Splitting the muscle fibers apart, rather than cutting the muscle causes less damage to the tissue and leads to faster recovery times and reduced patient discomfort. Also, sequential dilation provides an advantage in that it allows the surgeon to make an initially small incision, then gradually increase the size of the opening to the minimum size required for performing the surgical procedure, thus reducing tissue damage and speeding patient recovery time.

Certain spinal procedures, such as those developed by VertiFlex, Inc. and described in U.S. patent application Ser. No. 11/314,712 entitled "Systems and methods for posterior dynamic stabilization of the spine" filed on Dec. 20, 2005 and U.S. patent application Ser. No. 11/582,874 entitled "Minimally invasive tooling for delivery of interspinous spacer" filed on Oct. 18, 2006 and U.S. patent application Ser. No. 11/593,995 entitled "Systems and methods for posterior dynamic stabilization of the spine" filed on Nov. 7, 2006, U.S. patent application Ser. No. 12/148,104 entitled "Interspinous spacer" filed on Apr. 16, 2008, U.S. patent application Ser. No. 12/217,662 entitled "Interspinous spacer" filed on Jul. 8, 2008, U.S. patent application Ser. No. 12/220,427 entitled "Interspinous spacer" filed on Jul. 24, 2008, U.S. patent application Ser. No. 12/205,511 entitled "Interspinous spacer" filed on Sep. 5, 2008, U.S. patent application Ser. No. 12/338,793 entitled "Interspinous spacer" filed on Dec. 18, 2008, U.S. patent application Ser. No. 12/354,517 entitled "Interspinous spacer" filed on Jan. 15, 2009, all of which are incorporated herein by reference in their entireties, access the surgical site through tissue and through the supraspinous ligament, for example, for the insertion of a device, such as an interspinous spacer. Whereas the procedure may be performed in an open, mini-open or minimally invasive, percutaneous approach, penetrating the supraspinous ligament can be challenging as the ligamentous tissue is not only strong but also slippery. However, penetrating the supraspinous ligament particularly lends itself well to sequential dilation as the ligament is formed of a cord of substantially uniformly oriented fibrous strands that are advantageously capable of being split apart rather than transversely cut for minimizing trauma and increasing patient recovery time. Furthermore, approaching the interspinous process space through the supraspinous ligament, like the VertiFlex device, advantageously avoids the multifidus muscle and thereby preserves its critical function as a stabilizer of the lumbar spine. Because of the difficulties associated with penetrating ligament, there is a special need for a dilator and/or dilator system designed for accessing a surgical site through ligament such as the supraspinous or interspinous ligament. The current invention provides a dilator and dilator system for establishing an opening through ligament that may also be used in conjunction with minimally invasive, percutaneous procedures.

SUMMARY

According to one aspect of the invention, a dilator comprising a proximal portion and a distal portion interconnected by an elongated body portion is provided. At least a part of the distal portion has a cross-sectional area decreasing with distance towards the distal end. Two oppositely located channels are formed in the body portion and extend longitudinally into the distal portion.

A system comprising a dilator and a cannula is provided. The dilator comprises a proximal portion and a distal portion interconnected by an elongated body portion. At least a part of the distal portion has a cross-sectional area decreasing with distance towards the distal end. Two oppositely located channels are formed in the body portion and extend longitudinally into the distal portion. The cannula includes two oppositely located channels on the outer surface and has a passageway configured to receive the dilator.

A method is provided comprising the steps of inserting a dilator into a patient via a posterior midline approach between two adjacent spinous processes and distracting the adjacent spinous processes by advancing the dilator relative to the adjacent spinous processes.

BRIEF DESCRIPTION OF THE DRAWINGS

FIG. 2c is a perspective view of a distal end of a dilator according to the present invention.

DETAILED DESCRIPTION

While the description of the dilator system of this invention will be discussed primarily in relation to spinal surgery, it should be understood that the system will find use in other areas of surgery in which a surgeon wishes to gain access to an internal cavity by cutting the skin and enlarging an incision in a body wall so that surgical instruments can be inserted to perform a desired surgical procedure. For example, the dilator system may be used to create an incision to provide access to the posterior spine through which pedicle screws may be percutaneously installed in one or more selected vertebra. Alternatively, the dilator system may be used to create an incision to access an intervertebral disc space for performance of a minimally invasive discectomy procedure and/or spinal fusion procedure including the implantation of one or more intervertebral or interspinous process implants.

Figure 10:
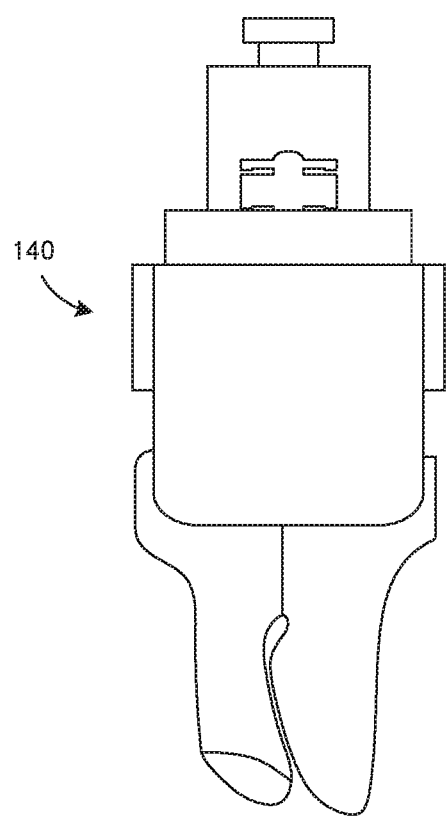
FIG. 10 is a side view of an implant.

Implants are inserted between adjacent spinous processes to distract the spine segments and maintain them in a position to relieve symptoms of spinal stenosis and other conditions that cause pain which is associated with the back. Such implants have a spacer which remains in place between the adjacent spinous processes. An opening is created in the supraspinous and/or interspinous ligament so that the implant (e.g., implant 140 of FIG. 10 and as described in U.S. Pat. No. 8,128,622) can be inserted. The dilators of the present invention are used to step dilate or gradually dilate body tissue, in particular, the supraspinous and/or interspinous ligament.

The dilator system of the present invention includes one or more dilators configured to work independently or in conjunction with one another. When used in conjunction with one another a first dilator is generally smaller in outer diameter or cross-sectional area than that of a second dilator which typically is also cannulated so that the second dilator fits over the first dilator to dilate tissue. It should be noted that the second dilator, in one variation, is not cannulated but is sized larger than the first dilator. In such a variation, the first dilator is removed and the second dilator is inserted to expand body tissue. In another variation, the first dilator is cannulated to be placed over a guide wire that is first positioned in the patient. In any of the variations disclosed herein, the first dilator may also be cannulated. Although in some cases two dilators are discussed it should be noted that more than two dilators may be employed in any of the variations disclosed herein. Furthermore, some of the distal ends of the dilators of the present invention are sufficiently sharp or manufactured with integrated knife points to cut tissue without a need for a separate instrument such as a scalpel to create an initial incision in the skin or ligament which is then expanded with the dilators, whereas other dilators of the present invention have a distal end that is too blunt and a separate instrument such as a scalpel is employed to create the first incision in the tissue or ligament.

Figure 1A:
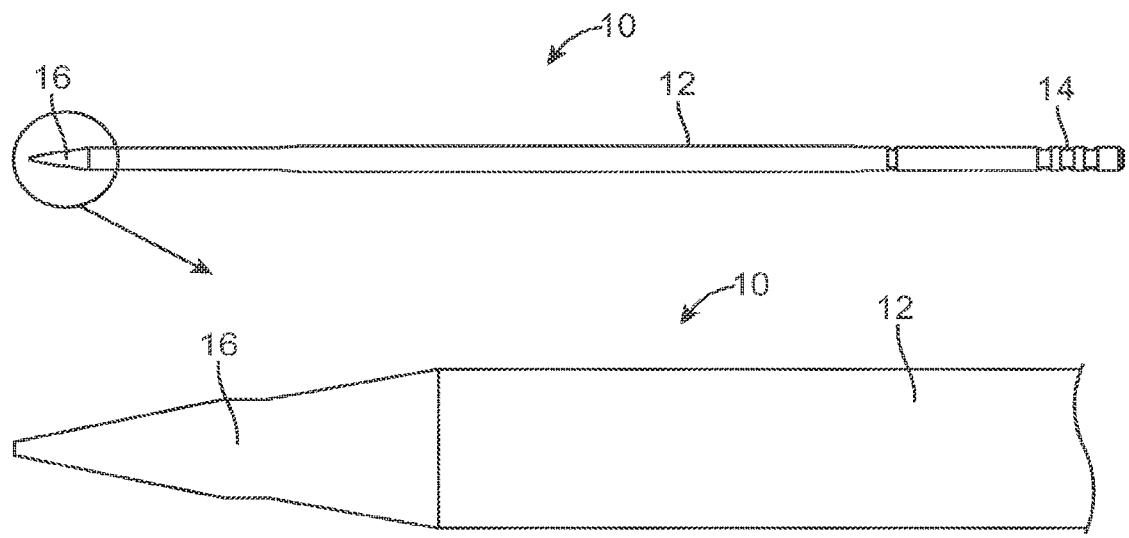
FIG. 1a is a side view of a dilator and an enlarged portion of the distal end of the dilator according to the present invention.
Figure 1B:
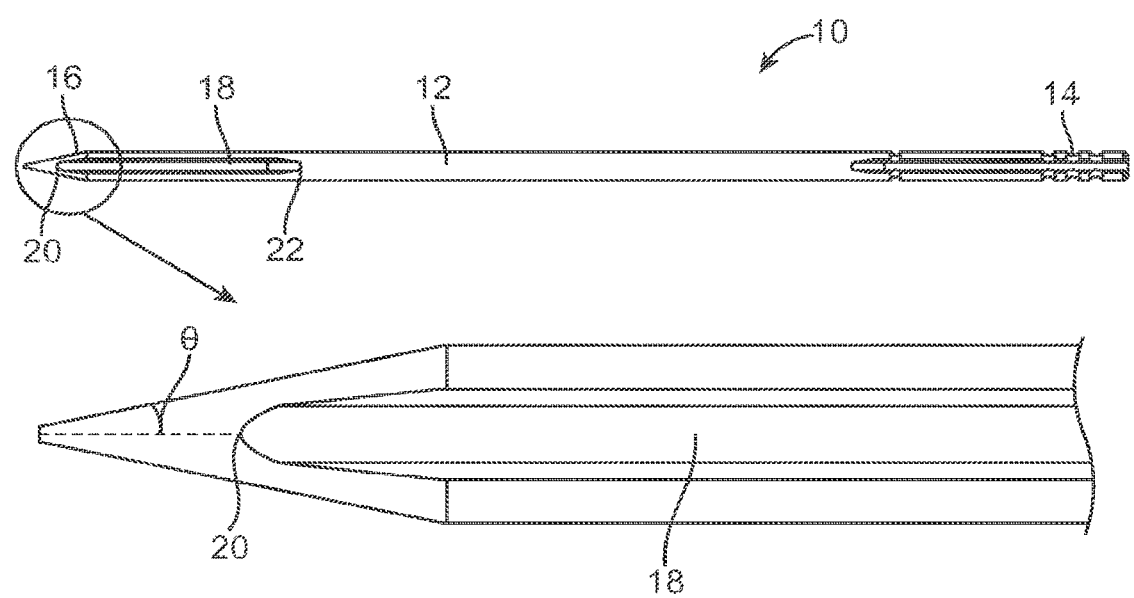
FIG. 1b is a top view of a dilator and an enlarged portion of the distal end of the dilator according to the present invention.
Figure 1C:
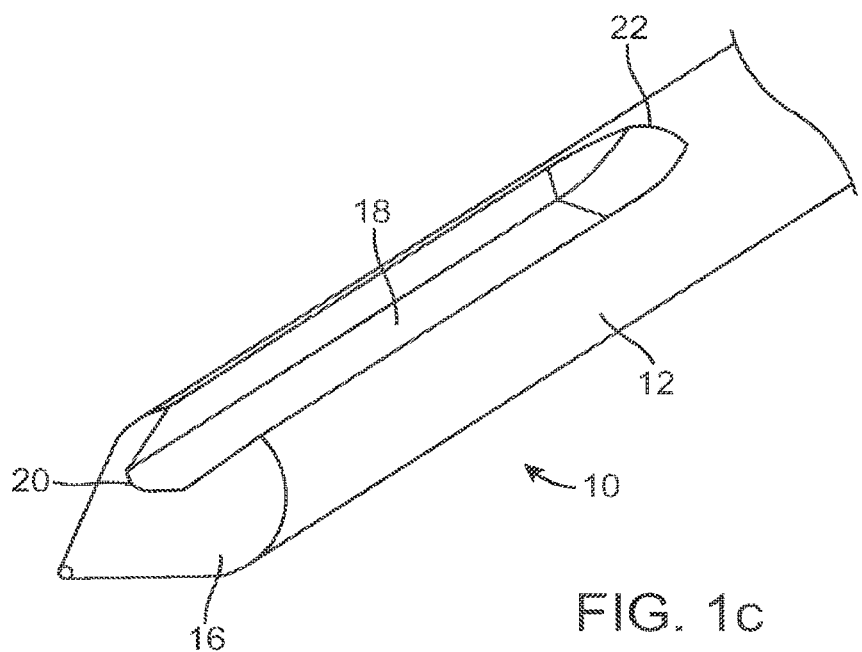
FIG. 1c is a perspective view of a distal end of a dilator according to the present invention.
Figure 1D:
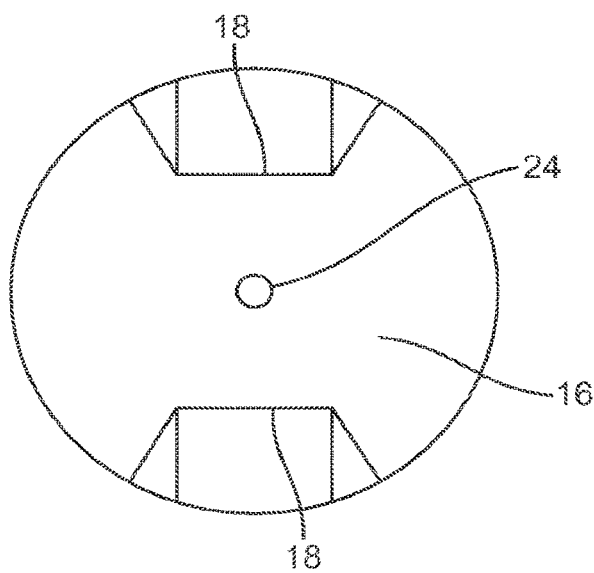
FIG. 1d is an end view of a distal end of a dilator according to the present invention.
Figure 1E:
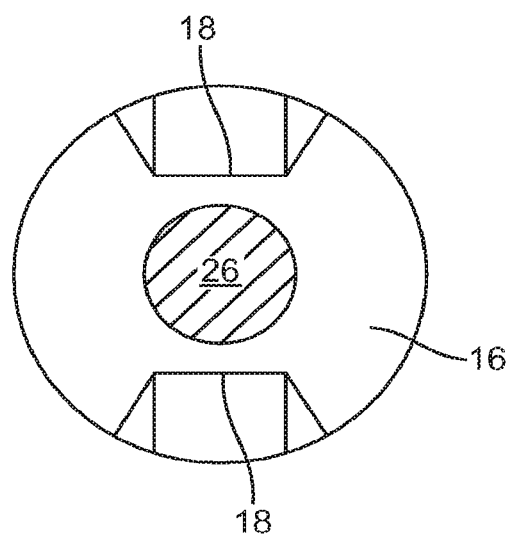
FIG. 1e is a cross-sectional view of the distal end of a dilator according to the present invention.

With reference to FIG. 1a, there is shown a dilator 10 according to the present invention. The dilator 10 has an elongated body 12, a proximal end 14 and a distal end 16. The dilator 10 includes a pair of channels 18 shown in FIGS. 1b, 1c and 1e that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. In one variation, the channel 18 has a flat base between two sidewalls. When inserted in a patient and aligned with the adjacent spinous processes, the channels 18 are advantageous for distracting the spinous processes apart as well as for keeping the dilator 10 in position between the spinous processes while being inserted especially in a "kissing" condition of the spine where the posterior tips of adjacent spinous processes are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12. In the embodiment shown in FIGS. 1a-1e, the distal end 16 portion has a cone shape shown in FIG. 1c. An end view of the distal end 16 is shown in FIG. 1d illustrating the tip or point 24 of the cone or bore 24 in a cannulated version of the dilator. When a cross-section of the distal end 16 is taken at a location distal to the channels 18 and perpendicular to the longitudinal axis of the dilator 10 as shown in FIG. 1e, the cross-sectional area 26 of the distal end 16 is circular in shape. The cone-shaped dilator of FIGS. 1a-1e is generally employed as a first dilator 10 and may be cannulated for passing over a guide wire or if used as a subsequent dilator for passing over a previous dilator. The cone-shaped dilator 10 shown in FIG. 1 punctures ligament and passes through soft tissue easily and therefore, it can be used as a first dilator in a minimally invasive percutaneous procedure without the need to first create a cut with a separate sharp edge such as a scalpel. A sharper tip formed by a distal end 16 with a more acute angle Θ (see FIG. 1b) will prevent the tip 24 from slipping off to the sides of the ligament.

Figure 2A:
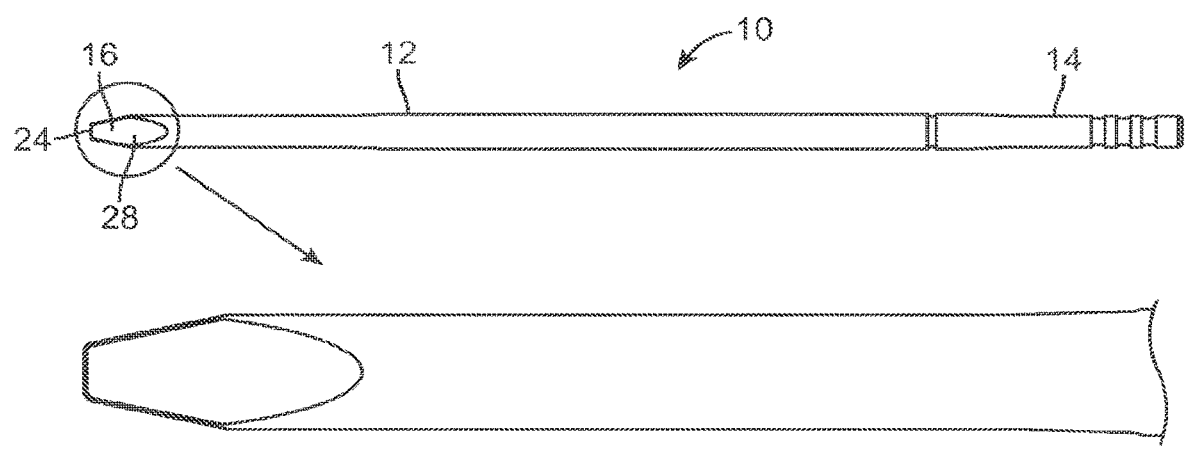
FIG. 2a is a side view of a dilator and an enlarged portion of the distal end of the dilator according to the present invention.
Figure 2B:
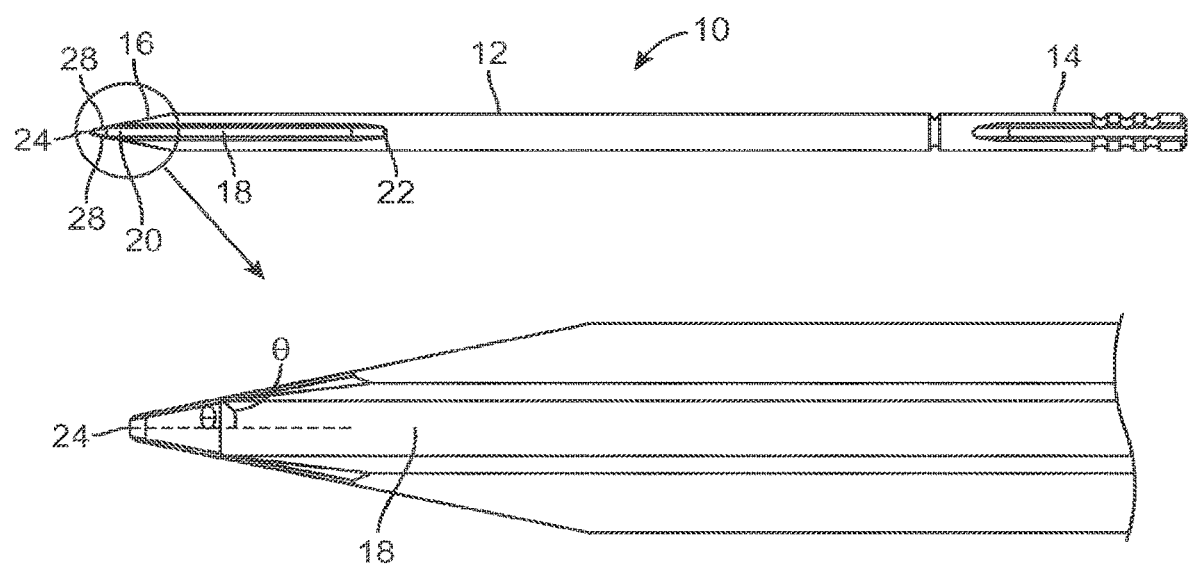
FIG. 2b is a top view of a dilator and an enlarged portion of the distal end of the dilator according to the present invention.
Figure 2D:
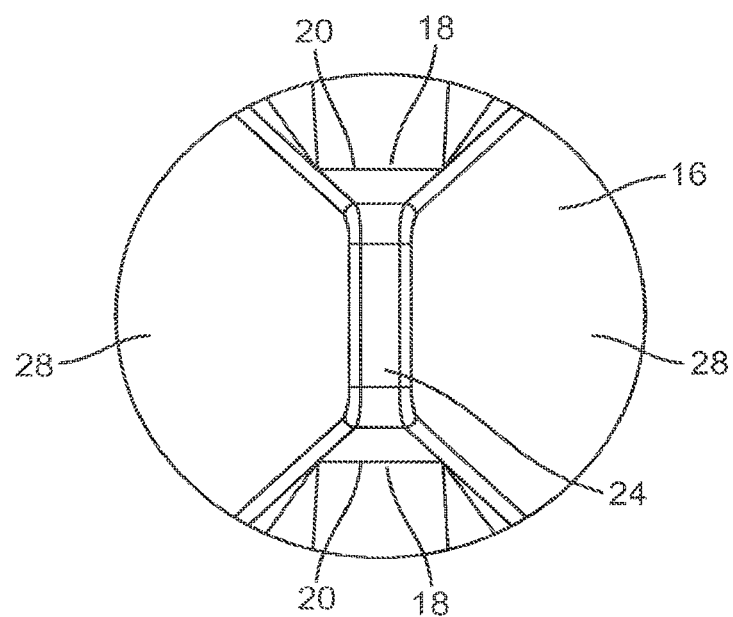
FIG. 2d is an end view of a distal end of a dilator according to the present invention.
Figure 2E:
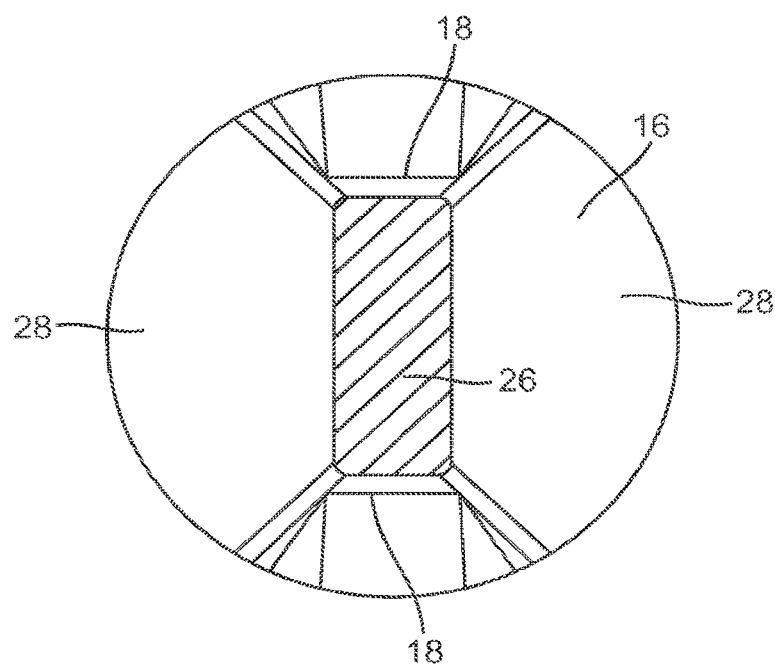
FIG. 2e is a cross-sectional view of the distal end of a dilator according to the present invention.

Turning now to FIGS. 2a-2e, there is shown another variation of a dilator 10 according to the present invention wherein like reference numbers are used to describe like parts. Referring first to FIG. 2a, the dilator 10 has an elongated body 12, a proximal end 14 and a distal end 16. The dilator 10 includes a pair of channels 18 shown in FIGS. 2b, 2c and 2e that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. When inserted in a patient and aligned with the adjacent spinous processes, the channels 18 are advantageous for distracting the spinous processes apart as well as for keeping the dilator 10 in position between adjacent spinous processes while being inserted especially in a "kissing" condition of the spine where the posterior tips of adjacent spinous processes are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12 and decreases toward the distal end 16. In the embodiment shown in FIGS. 2a-2e, the distal end 16 portion has a wedge shape formed by two substantially flat faces 28 that angle towards each other at the distal end 16 and form a line or rectangular tip 24 shown in FIG. 2d. An end view of the distal end 16 is shown in FIG. 2d illustrating the line or rectangular tip 24 of the wedge. A cannulated variation of the dilator 10 is not shown but is within the scope of the present invention. When a cross-section of the distal end 16 is taken at a location distal to the channels 18 and perpendicular to the longitudinal axis of the dilator 10 as shown in FIG. 2e, the cross-sectional area 26 of the distal end 16 is rectangular in shape. The wedge-shaped dilator of FIGS. 2a-2e is generally employed as a first dilator 10 and may be cannulated for passing over a guide wire or if used as a subsequent dilator for passing over a previous dilator. The distal end 16 is positioned in the patient such that the length of the tip 24 is aligned along the cephalad-caudal direction when puncturing the supraspinous ligament or otherwise aligned substantially parallel to the fibrous strands of the ligament. The wedge-shaped dilator 10 shown in FIGS. 2a-2e does not puncture ligament as readily as the dilator 10 of FIGS. 1a-1e and hence, is typically used in conjunction with a scalpel or other sharp edge, for example, to create a small opening in the ligament prior to insertion of the dilator 10 of FIGS. 2a-2e which then splits the ligament to create a larger opening as it is inserted. For these reasons, the dilator of FIGS. 2a-2e is generally used as a first dilator in a mini-open or open procedure in which direct visual access is gained and a sharp edge is used to first create a cut. The line or rectangular shaped point 24 is centered as seen in FIGS. 2d and 2e and therefore advantageously assists in centering the location of the splitting on the ligament. It should be noted that a sharper tip may be formed by a distal end 16 with a more acute angle Θ (see FIG. 2b) thereby, creating or approaching a knife-like edge that can pierce the ligament without first using a sharp edge and therefore well suited for truly percutaneous procedures.

Figure 3A:
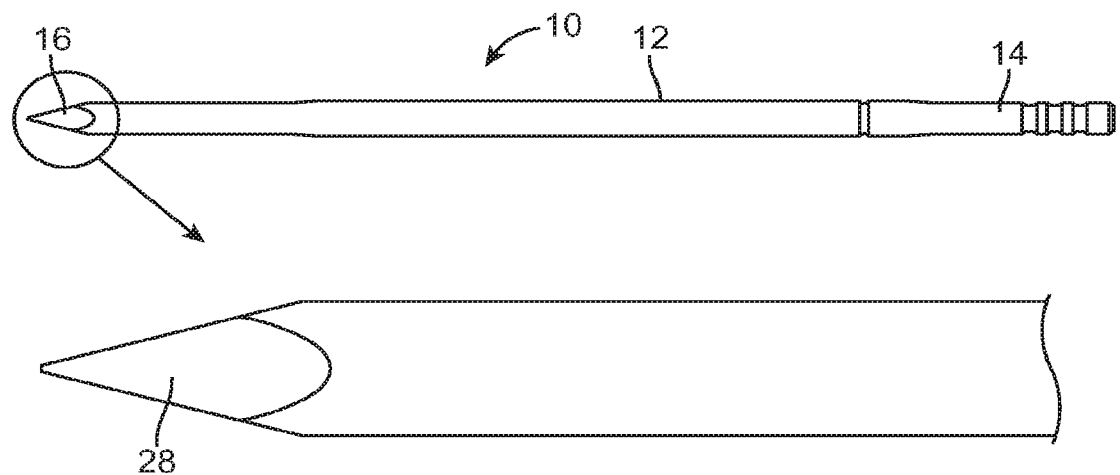
FIG. 3a is a side view of a dilator and an enlarged portion of the distal end of the dilator according to the present invention.
Figure 3B:
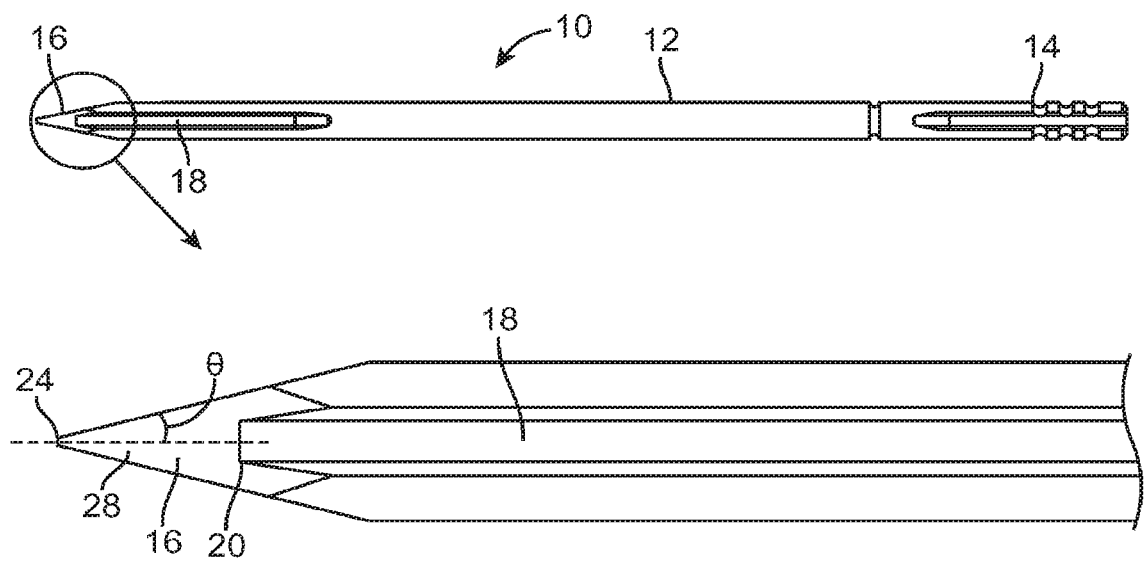
FIG. 3b is a top view of a dilator and an enlarged portion of the distal end of the dilator according to the present invention.
Figure 3C:
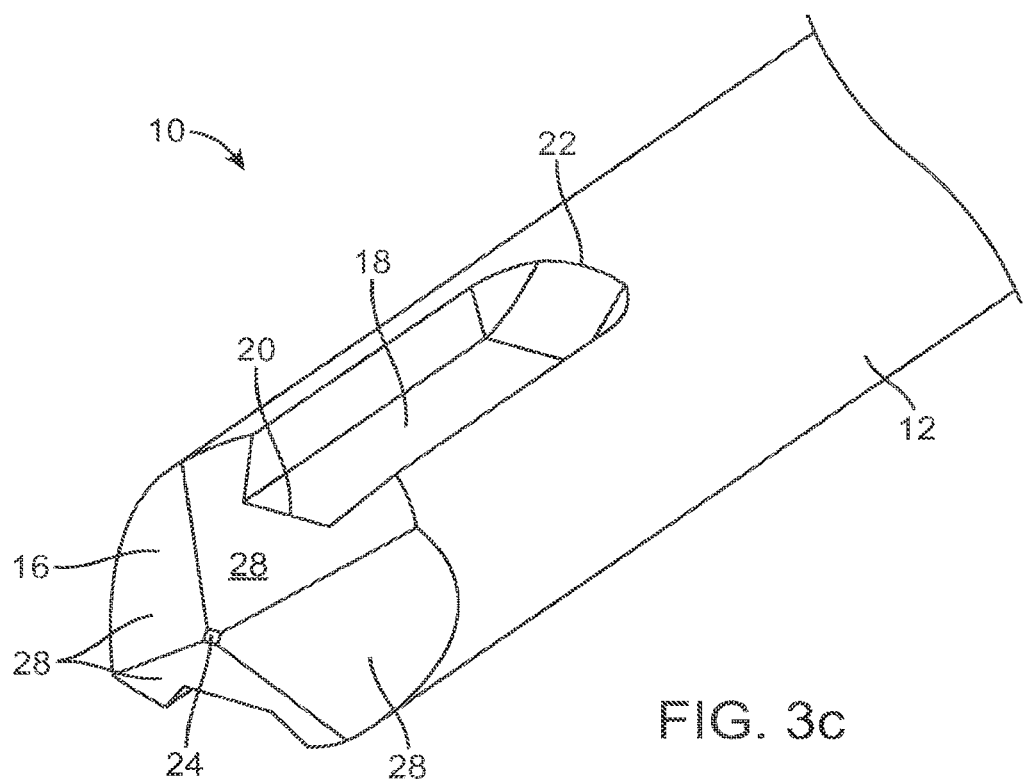
FIG. 3c is a perspective view of a distal end of a dilator according to the present invention.
Figure 3D:
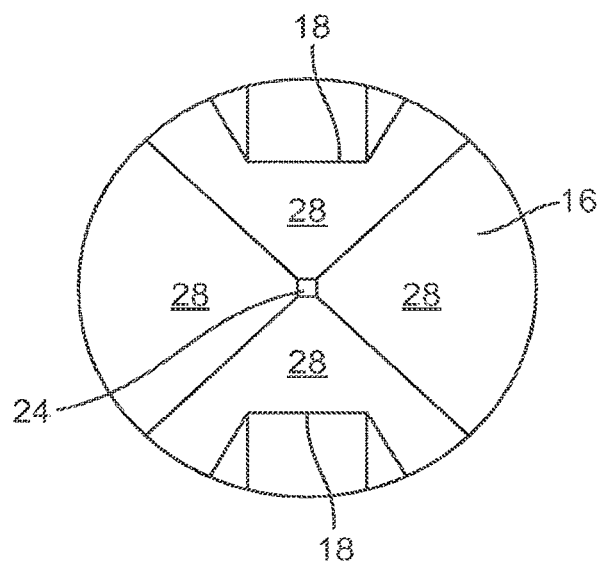
FIG. 3d is an end view of a distal end of a dilator according to the present invention.
Figure 3E:
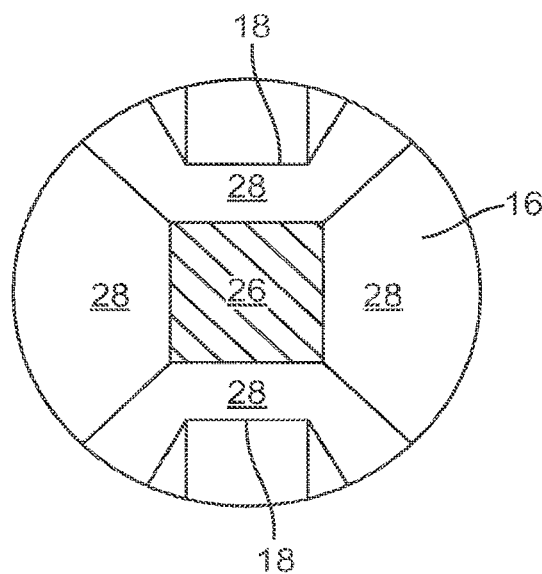
FIG. 3e is a cross-sectional view of the distal end of a dilator according to the present invention.

Turning now to FIGS. 3a-3e, there is shown another variation of a dilator 10 according to the present invention wherein like reference numbers are used to describe like parts. Referring first to FIG. 3a, the dilator 10 has an elongated body 12, a proximal end 14 and a distal end 16. The dilator 10 includes a pair of channels 18 shown in FIGS. 3b, 3c, 3d and 3e that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. When inserted in a patient and aligned with the adjacent spinous processes, the channels 18 are advantageous for distracting the spinous processes apart as well as for keeping the dilator 10 in position between the spinous processes while being inserted especially in a "kissing" condition of the spine where the posterior tips of adjacent spinous processes are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12 and decreases towards the distal end 16. In the embodiment shown in FIGS. 3a-3e, the distal end 16 portion has a pyramid shape formed by four substantially flat faces 28 that angle towards each other at the distal end 16 and meet at a tip 24 shown in FIGS. 3c and 3d. An end view of the distal end 16 is shown in FIG. 3d illustrating the tip 24 of the pyramid-shaped distal end 16. A cannulated variation of the dilator 10 is not shown but is within the scope of the present invention wherein the tip 24 would include an opening. When a cross-section of the distal end 16 is taken at a location distal to the channels 18 and perpendicular to the longitudinal axis of the dilator 10 as shown in FIG. 3e, the cross-sectional area 26 of the distal end 16 is substantially square in shape. The pyramid-shaped dilator of FIGS. 3a-3e is generally employed as a first dilator 10 and may be cannulated for passing over a guide wire or if used as a subsequent dilator for passing over a previous dilator. The pyramid-shaped dilator 10 shown in FIGS. 3a-3e can puncture ligament and pass through soft tissue and hence, is generally used as a first dilator in a minimally invasive percutaneous procedure without the need to first create a cut with a separate sharp edge such as a scalpel. A sharper tip formed by a distal end 16 with a more acute angle Θ (see FIG. 3b) will prevent the tip 24 from slipping off to the sides of the ligament.

Figure 4A:
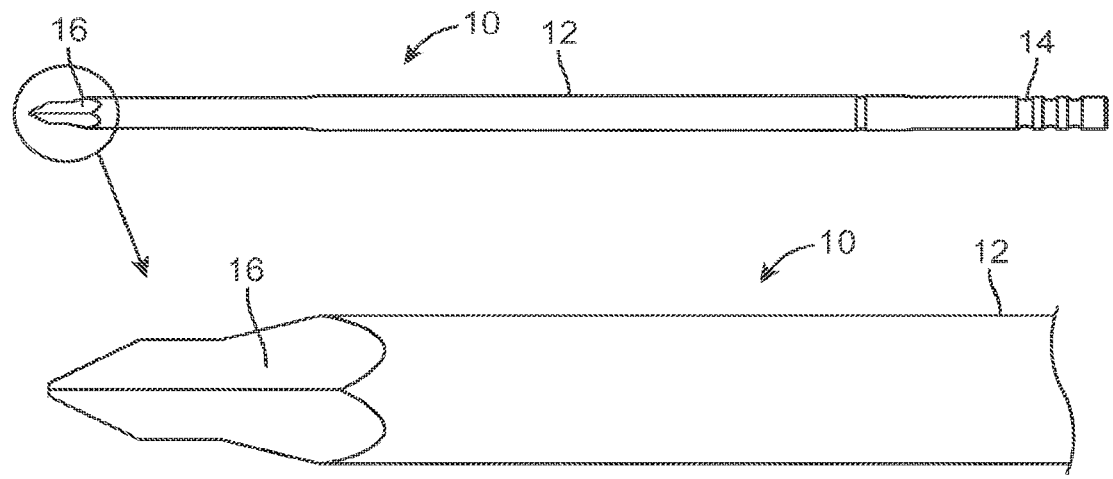
FIG. 4a is a side view of a dilator and an enlarged portion of the distal end of the dilator according to the present invention.
Figure 4B:
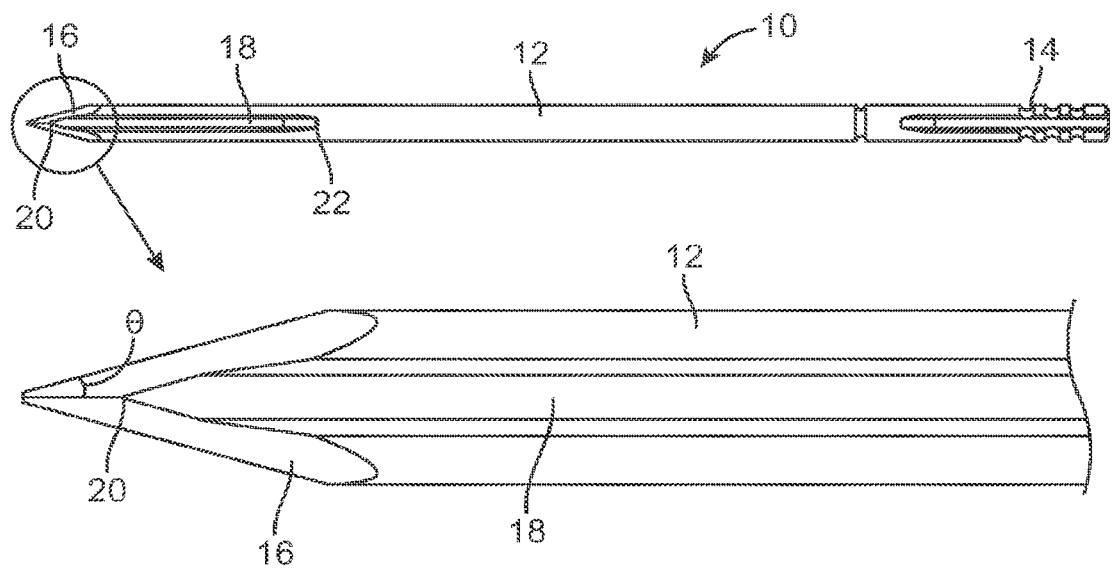
FIG. 4b is a top view of a dilator and an enlarged portion of the distal end of the dilator according to the present invention.
Figure 4C:
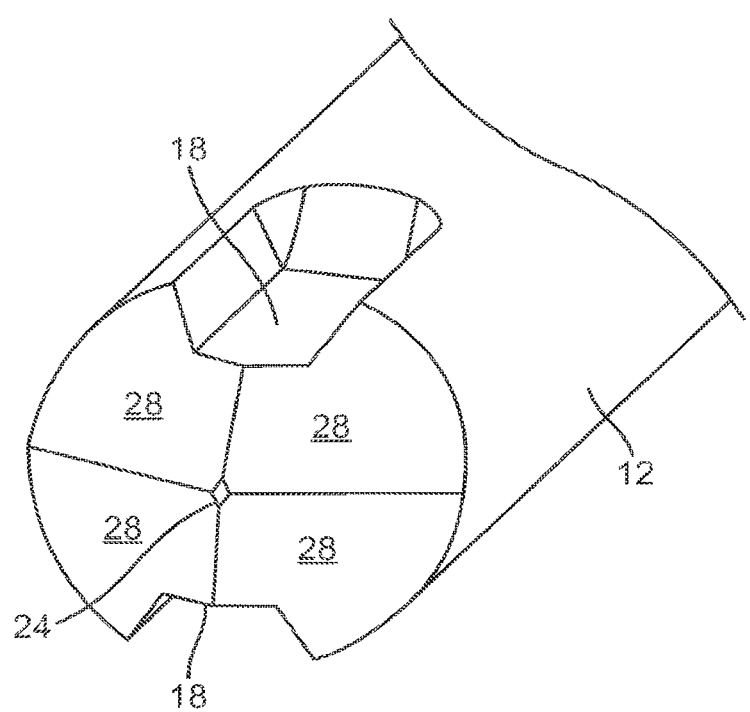
FIG. 4c is a perspective view of a distal end of a dilator according to the present invention.
Figure 4D:
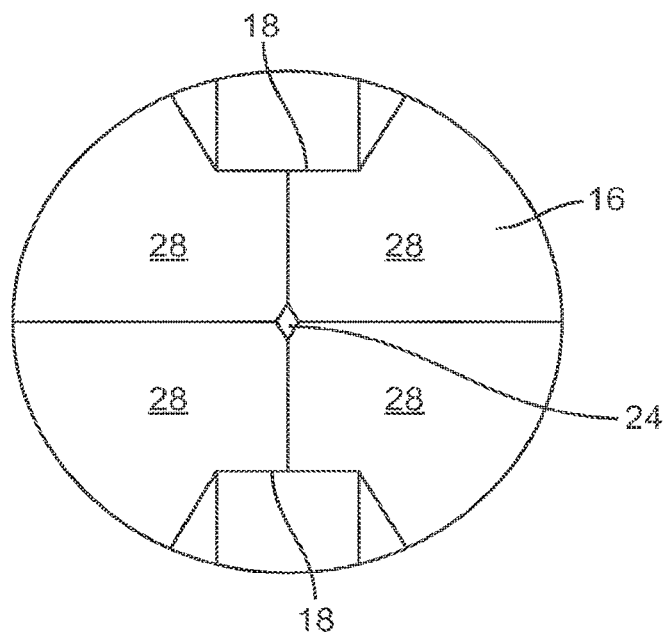
FIG. 4d is an end view of a distal end of a dilator according to the present invention.
Figure 4E:
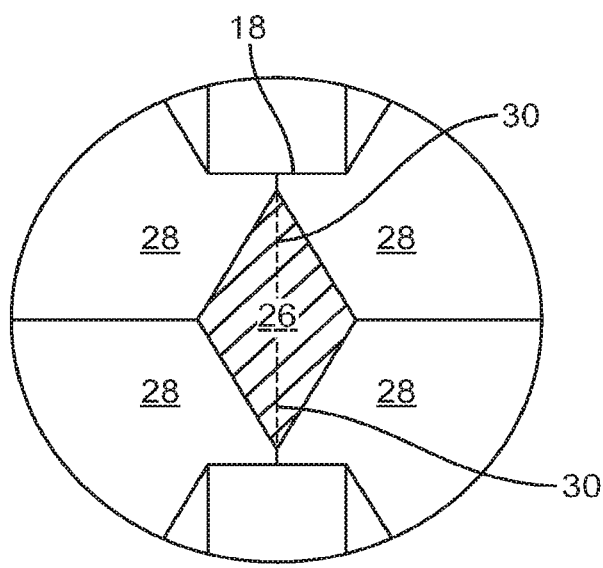
FIG. 4e is a cross-sectional view of the distal end of a dilator according to the present invention.

Turning now to FIGS. 4a-4e, there is shown another variation of a dilator 10 according to the present invention wherein like reference numbers are used to describe like parts. Referring first to FIG. 4a, the dilator 10 has an elongated body 12, a proximal end 14 and a distal end 16. The dilator 10 includes a pair of channels 18 shown in FIGS. 4b, 4c, 4d and 4e that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. When inserted in a patient and aligned with the adjacent spinous processes, the channels 18 are advantageous for distracting the spinous processes apart as well as for keeping the dilator 10 in position between the spinous processes while being inserted especially in a "kissing" condition of the spine where the posterior tips of adjacent spinous processes are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12 and decreases toward the distal end 16. In the embodiment shown in FIGS. 4a-4e, the distal end 16 portion has a pyramid shape formed by four substantially flat faces 28 that angle towards each other at the distal end 16 and form a tip 24 shown in FIG. 4d. An end view of the distal end 16 is shown in FIG. 4d illustrating the tip 24 of the pyramid. A cannulated variation of the dilator 10 is not shown but is within the scope of the present invention wherein the tip 24 would include an opening. When a cross-section of the distal end 16 is taken at a location distal to the channels 18 and perpendicular to the longitudinal axis of the dilator 10 as shown in FIG. 4e, the cross-sectional area 26 of the distal end 16 is a quadrilateral and, in the variation shown in FIG. 4e, the quadrilateral is a rhombus in which one of the diagonals 30 or the longest diagonal 30 is aligned with the channels 18 as opposed to the variation of FIGS. 3a-3e in which none of the diagonals are aligned with the channels 18. It is the intersection of two faces 28 that align with one channel 18 and the intersection of opposite two faces 28 that align with the other channel 18. In a variation in which no channels 18 are included, the difference between the dilator of FIGS. 3a-3e is in the shape of the quadrilateral. The pyramid-shaped dilator of FIGS. 4a-4e is generally employed as a first dilator 10 and may be cannulated for passing over a guide wire or if used as a subsequent dilator for passing over a previous dilator. The distal end 16 is positioned in the patient such that one of the diagonals or longest diagonal 30 is aligned along the cephalad-caudal direction when puncturing the supraspinous ligament or otherwise aligned substantially parallel to the fibrous strands of the ligament such that the intersection of faces 28 form an edge along which ligament is split. The pyramid-shaped dilator 10 shown in FIGS. 4a-4e in either the channeled or non-channeled variations, splits ligament more readily than either of the channeled or non-channeled variations of the dilator 10 of FIGS. 3a-3e where the intersections of faces 28 are not aligned with the channels 18 or does not have a diagonal 30 that is longer relative to the other diagonal 30 which can be aligned with the fibrous ligament strands for easier splitting. The variation of FIGS. 4a-4e can be used with or without a scalpel or other sharp edge, for example, to create a small opening in the ligament prior to insertion of the dilator 10 of FIGS. 4a-4e which then splits the ligament to create a larger opening as it is inserted. The intersection of faces 28 or diagonal 30, when aligned substantially parallel to the ligament strands, assist in centering the location of the splitting on the ligament. It should be noted that a sharper tip, intersection or diagonal may be formed by a distal end 16 with a more acute angle Θ (see FIG. 4b) thereby, creating or approaching a knife-like edge that can pierce the ligament without first using a sharp edge and therefore well suited for percutaneous procedures.

Figure 5A:
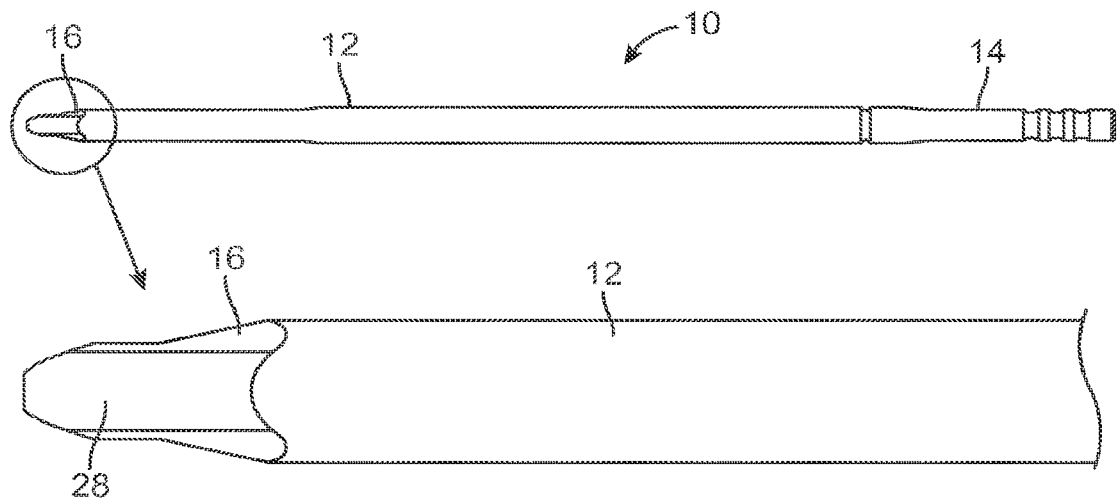
FIG. 5a is a side view of a dilator and an enlarged portion of the distal end of the dilator according to the present invention.
Figure 5B:
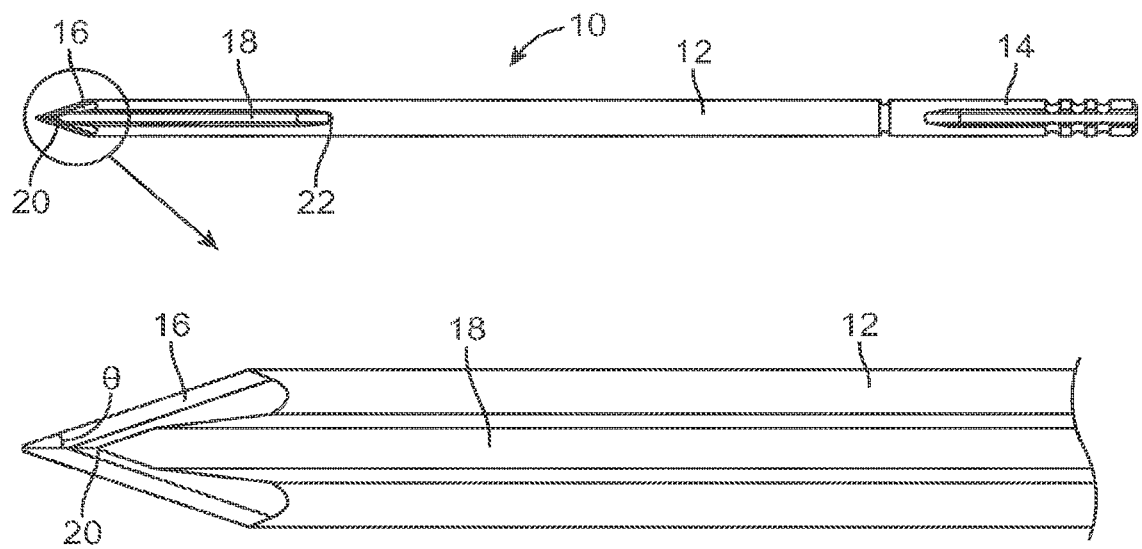
FIG. 5b is a top view of a dilator and an enlarged portion of the distal end of the dilator according to the present invention.
Figure 5C:
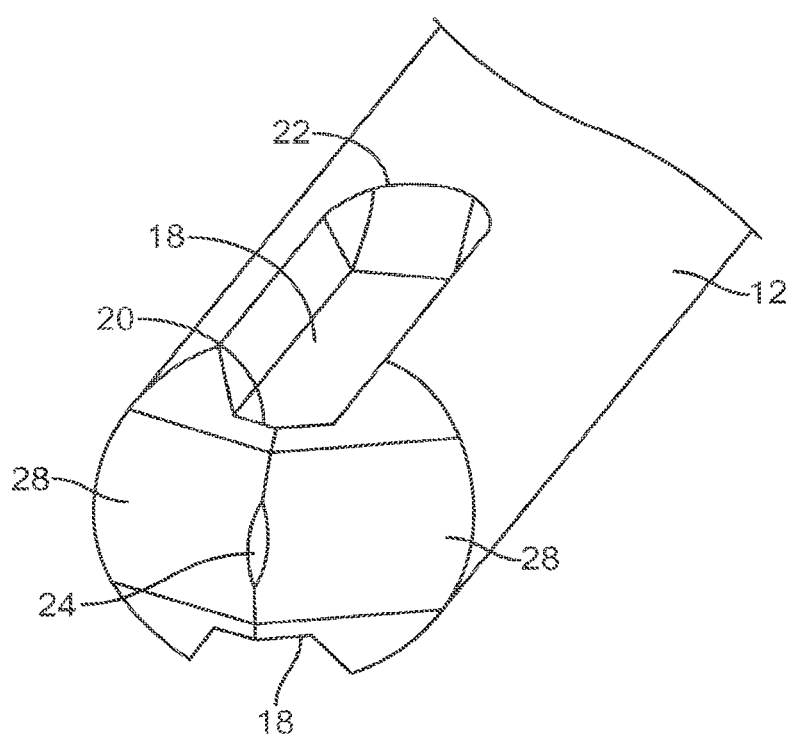
FIG. 5c is a perspective view of a distal end of a dilator according to the present invention.
Figure 5D:
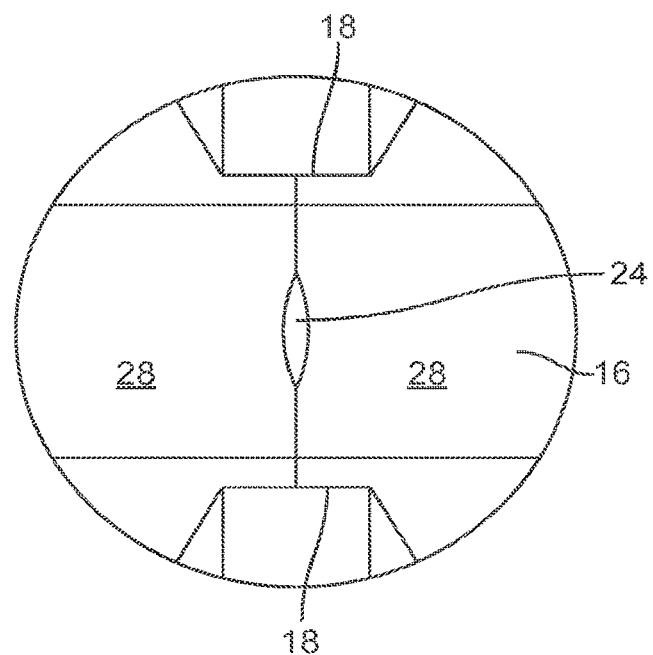
FIG. 5d is an end view of a distal end of a dilator according to the present invention.
Figure 5E:
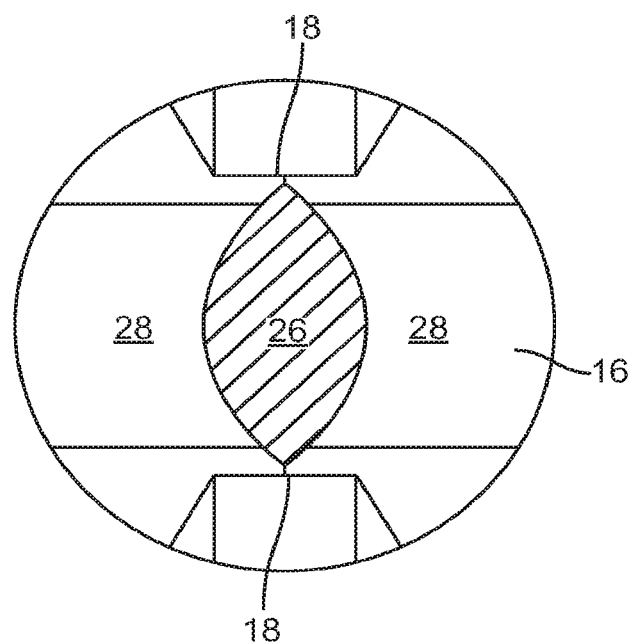
FIG. 5e is a cross-sectional view of the distal end of a dilator according to the present invention.

Turning now to FIGS. 5a-5e, there is shown another variation of a dilator 10 according to the present invention wherein like reference numbers are used to describe like parts. Referring first to FIG. 5a, the dilator 10 has an elongated body 12, a proximal end 14 and a distal end 16. The dilator 10 includes a pair of channels 18 shown in FIGS. 5b, 5c, 5d and 5e that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. When inserted in a patient and aligned with the adjacent spinous processes, the channels 18 are advantageous for distracting the spinous processes apart as well as for keeping the dilator 10 in position between the spinous processes while being inserted especially in a "kissing" condition of the spine where the posterior tips of adjacent spinous processes are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12 and decreases toward the distal end 16. In the embodiment shown in FIGS. 5a-5e, the distal end 16 portion has two curved faces 28 that angle towards each other at the distal end 16 and form a tip 24 shown in FIG. 5d. An end view of the distal end 16 is shown in FIG. 5d illustrating the tip 24. A cannulated variation of the dilator 10 is not shown but is within the scope of the present invention wherein the tip 24 would include an opening. In yet another variation, the tip 24 includes an opening to a blade housing through which a blade may extend. The blade (not shown) may also be retractable. When a cross-section of the distal end 16 is taken at a location distal to the channels 18 and perpendicular to the longitudinal axis of the dilator 10 as shown in FIG. 5e, the cross-sectional area 26 of the distal end 16 is comprised of an area bounded by two curved lines in which the length is aligned with the channels 18. It is the intersections of two faces 28 that align with one channel 18. In a variation in which no channels 18 are included, the length is aligned with the length of the ligament. The dilator 10 of FIGS. 5a-5e is generally employed as a first dilator 10 and may be cannulated for passing over a guide wire or if used as a subsequent dilator for passing over a previous dilator. The distal end 16 is positioned in the patient such that the length of the tip 24 is aligned along the cephalad-caudal direction when puncturing the supraspinous ligament or otherwise aligned substantially parallel to the fibrous strands of the ligament or to the ligament itself such that the intersections of faces 28 form an edge along which ligament is split. The variation of FIGS. 5a-5e can be used with or without a scalpel or other sharp edge, for example, to create a small opening in the ligament prior to insertion of the dilator 10 of FIGS. 5a-5e which then splits the ligament to create a larger opening as it is inserted. The intersection of faces 28 when aligned substantially parallel to the ligament strands, assist in centering the location of the splitting on the ligament. It should be noted that a sharper tip, intersection or diagonal may be formed by a distal end 16 with a more acute angle Θ (see FIG. 5b) thereby, creating or approaching a knife-like edge that can pierce the ligament without first using a sharp edge and therefore well suited for percutaneous procedures.

Figure 6A:
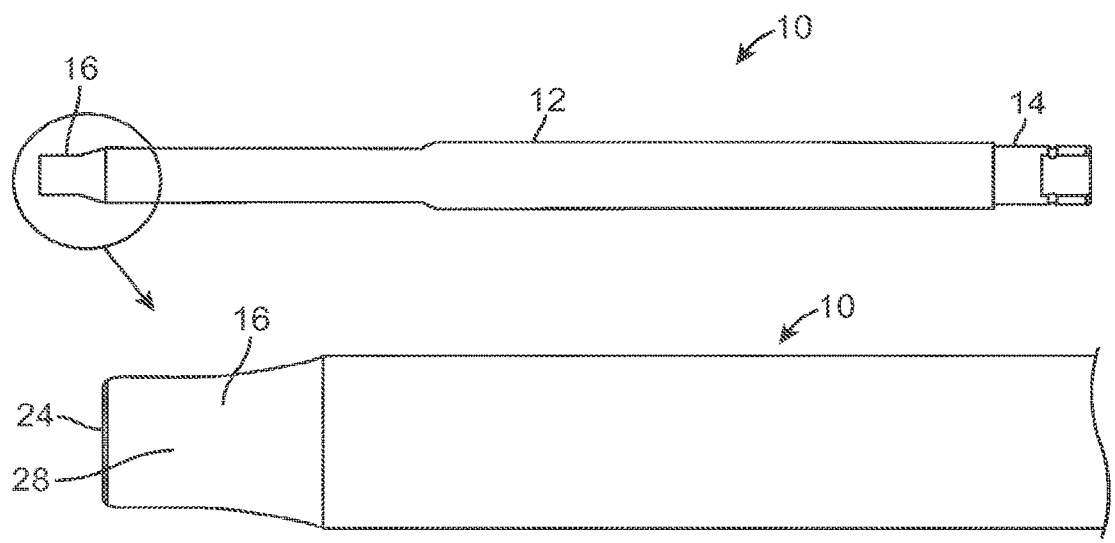
FIG. 6a is a side view of a dilator and an enlarged portion of the distal end of the dilator according to the present invention.
Figure 6B:
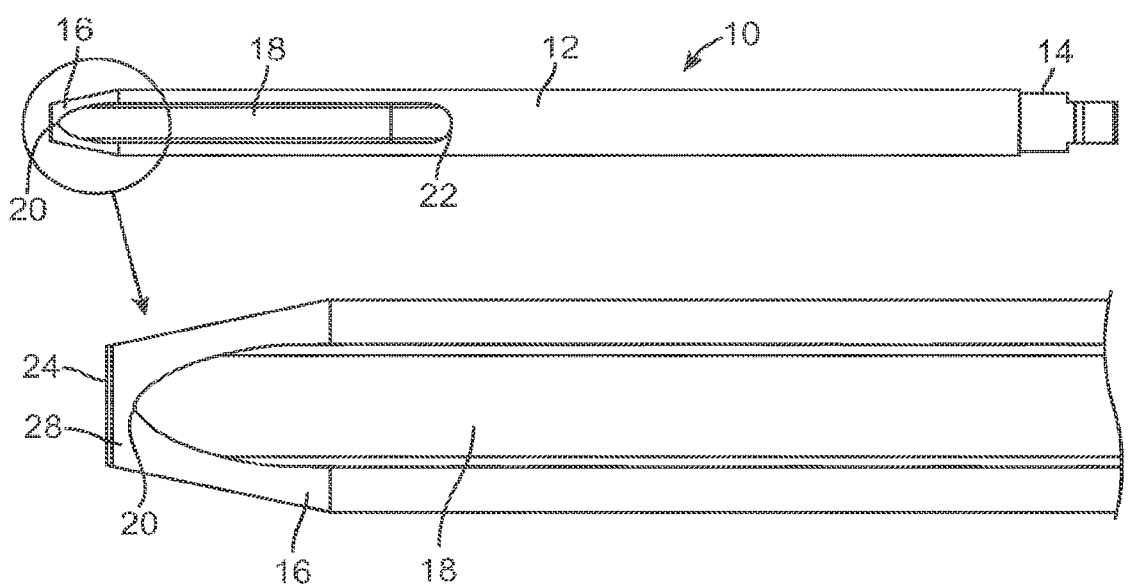
FIG. 6b is a top view of a dilator and an enlarged portion of the distal end of the dilator according to the present invention.
Figure 6C:
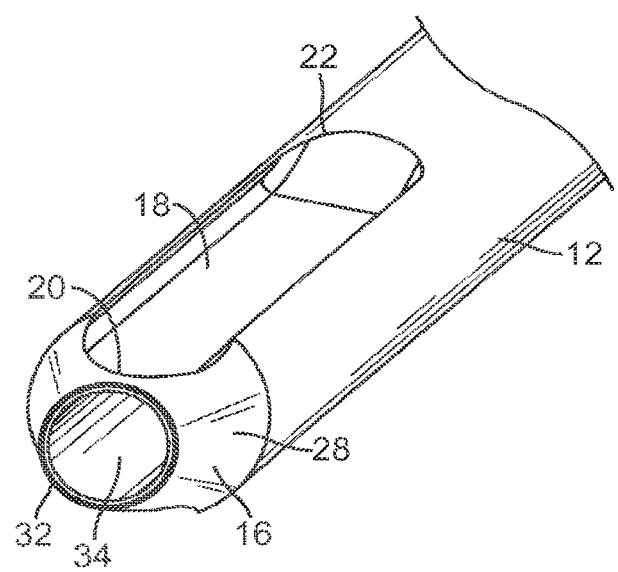
FIG. 6c is a perspective view of a distal end of a dilator according to the present invention.
Figure 6D:
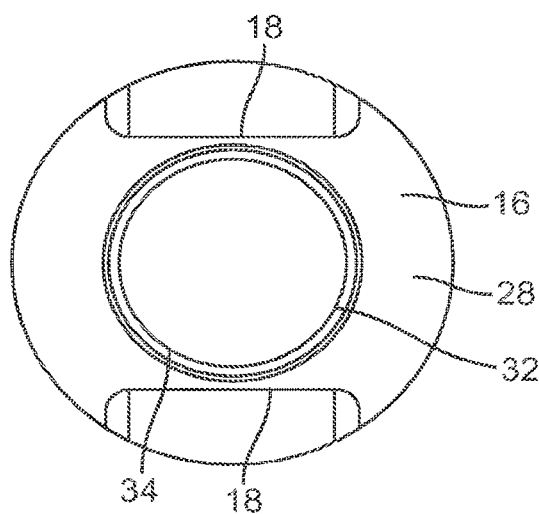
FIG. 6d is an end view of a distal end of a dilator according to the present invention.

Turning now to FIGS. 6a-6d, there is shown another variation of a dilator 10 according to the present invention wherein like reference numbers are used to describe like parts. Referring first to FIG. 6a, the dilator 10 has an elongated body 12, a proximal end 14 and a distal end 16. The dilator 10 includes a pair of channels 18 shown in FIGS. 6b, 6c and 6d that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. When inserted in a patient and aligned with the adjacent spinous processes, the channels 18 are advantageous for distracting the spinous processes apart as well as for keeping the dilator 10 in position between the spinous processes while being inserted especially in a "kissing" condition of the spine where the posterior tips of adjacent spinous processes are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12 and decreases toward the distal end 16. In the embodiment shown in FIGS. 6a-6d, the distal end 16 portion has a surface 28, that may also be curved that angles toward the distal end 16 and forms an opening 32 at tip 24 shown in FIGS. 6c and 6d. An end view of the distal end 16 is shown in FIG. 6d illustrating the opening 32 that forms distal end of the cannulation or bore 34 running along at least part of the length of the dilator 10. Because of the central bore 34 is sized to received therein a smaller dilator 10 such as any of the dilators described above in FIGS. 1-5, the dilator 10 of FIGS. 6a-6d is generally employed as a second dilator 10 or dilator 10 subsequent for passing over a previous dilator. The distal end 16 is positioned over a previous dilator 10 in the patient such that the channels 18 are aligned generally perpendicular to the cephalad-caudal direction when puncturing the supraspinous ligament or otherwise aligned substantially perpendicular to the fibrous strands of the ligament or to the ligament itself. When inserted, the cannula of FIGS. 6a-6d continues to distract the spinous processes as they ride in the channels 18 with the channels 18 helping with maintaining the proper orientation of the dilators 10 between the spinous processes. In one variation, the channels 18 are ramped or angled towards the distal end to improve upon the distraction action provided by the dilator.

Figure 7A:
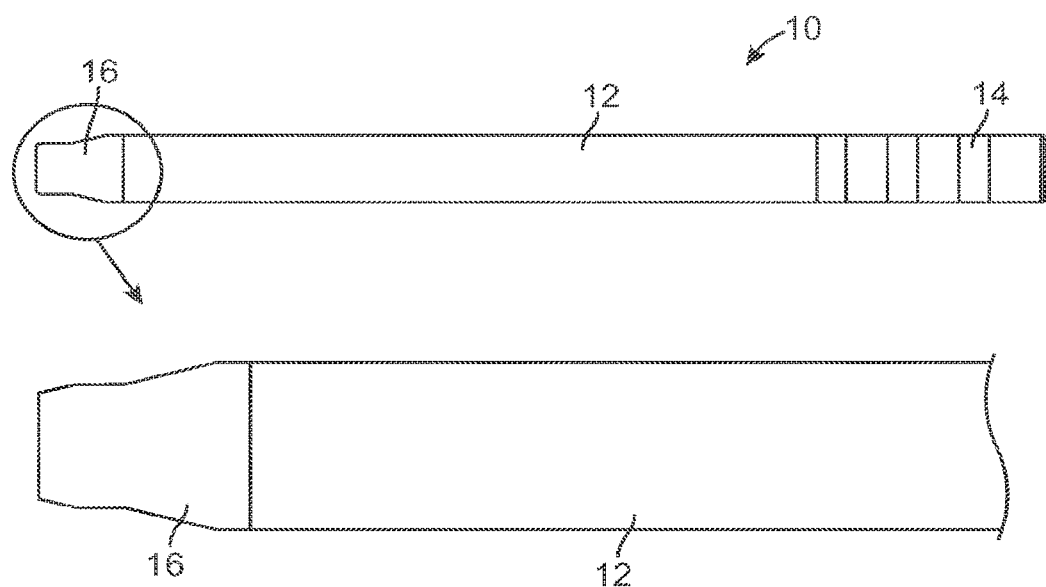
FIG. 7a is a side view of a dilator and an enlarged portion of the distal end of the dilator according to the present invention.
Figure 7B:
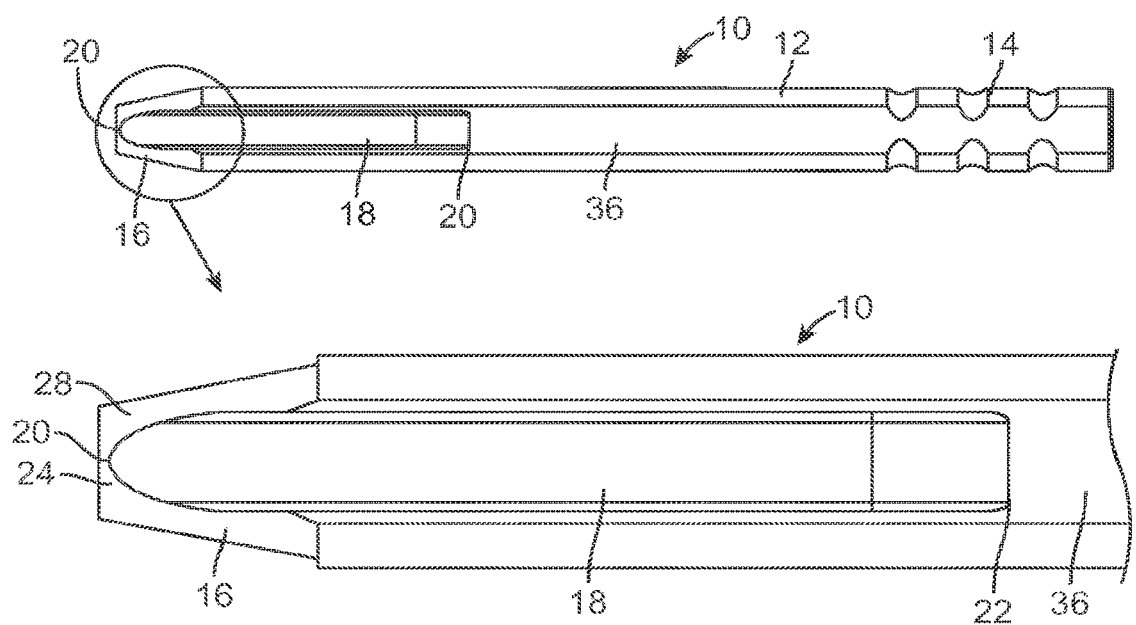
FIG. 7b is a top view of a dilator and an enlarged portion of the distal end of the dilator according to the present invention.
Figure 7C:
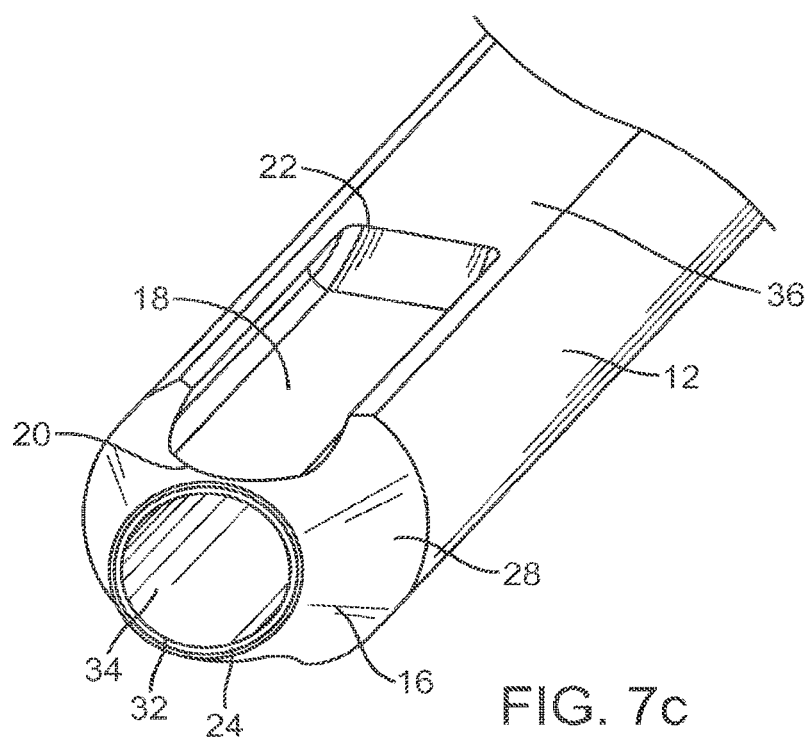
FIG. 7c is a perspective view of a distal end of a dilator according to the present invention.
Figure 7D:
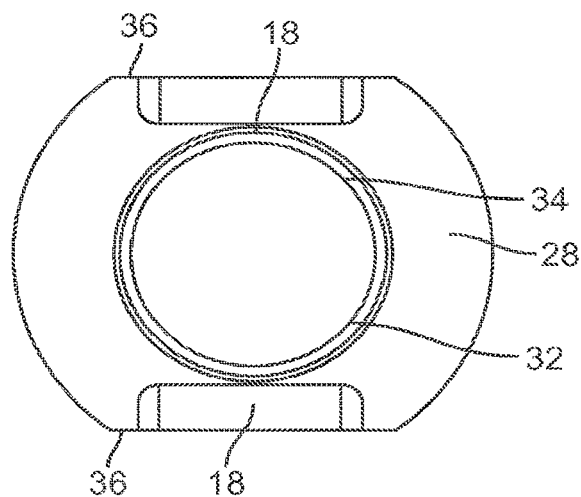
FIG. 7d is an end view of a distal end of a dilator according to the present invention.

Turning now to FIGS. 7a-7d, there is shown another variation of a dilator 10 according to the present invention wherein like reference numbers are used to describe like parts. Referring first to FIG. 7a, the dilator 10 has an elongated body 12, a proximal end 14 and a distal end 16. The dilator 10 includes a pair of channels 18 shown in FIGS. 7b, 7c and 7d that are oppositely located from each other and run parallel to the longitudinal axis of the dilator 10. The distal end 20 of the channel 18 commences in the distal end 16 and the proximal end 22 of the channel 18 ends in the body 12 portion of the dilator 10. In one variation, the channel 18 includes a flat base between two sidewalls. When inserted in a patient and aligned with the adjacent spinous processes, the channels 18 are advantageous for distracting the spinous processes apart as well as for keeping the dilator 10 in position between the spinous processes while being inserted especially in a "kissing" condition of the spine where the posterior tips of adjacent spinous process are in close proximity, touch or "kiss". In one variation, the channels 18 are absent from the dilator 10. The distal end 16 of the dilator 10 is a tapered portion where the diameter or cross-sectional area is less than the diameter or cross-sectional area of the body portion 12 and decreases toward the distal end 16. In the embodiment shown in FIGS. 7a-7d, the distal end 16 portion has a surface 28 that may also be curved that angles toward the distal end 16 and forms an opening 32 at tip 24 shown in FIGS. 7c and 7d. An end view of the distal end 16 is shown in FIG. 7d illustrating the opening 32 that forms distal end of the cannulation or bore 34 running along at least part of the length of the dilator 10. Because of the central bore 34 is sized to received therein a smaller dilator 10 such as any of the dilators described above in FIGS. 1-5, the dilator 10 of FIGS. 7a-7d is generally employed as a second dilator 10 or dilator 10 subsequent for passing over a previous dilator. The distal end 16 is positioned over a previous dilator 10 in the patient such that the channels 18 are aligned generally perpendicular to the cephalad-caudal direction when puncturing the supraspinous ligament or otherwise aligned substantially perpendicular to the fibrous strands of the ligament or to the ligament itself. The dilator of FIGS. 7a-7d further includes a pair of oppositely located flats 36 that are aligned with the channels 18. At least part of the channel 18 is formed in the flats 36 and in one variation, the flat 36 is substantially parallel to the flat base of the channel 18. The flats 36 create a lower profile for the dilator 10 which is advantageous for insertion between closely spaced spinous processes. When inserted, the cannula of FIGS. 7a-7d continues to distract the spinous processes as they ride in the channels 18 with the channels 18 helping with maintaining the proper orientation of the dilators 10 between the spinous processes.

Figure 8A:
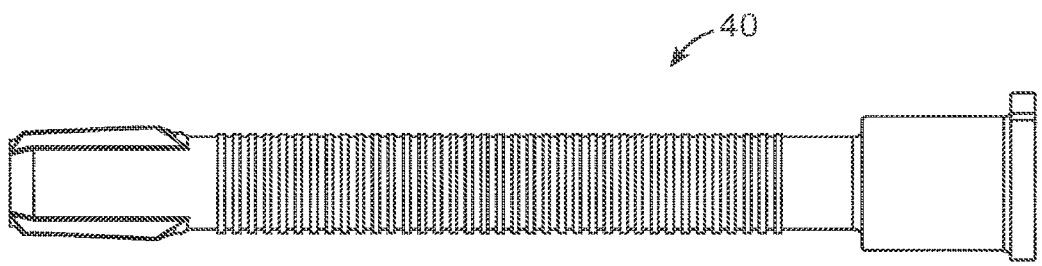
FIG. 8a is a side view of a cannula according to the present invention.
Figure 8B:
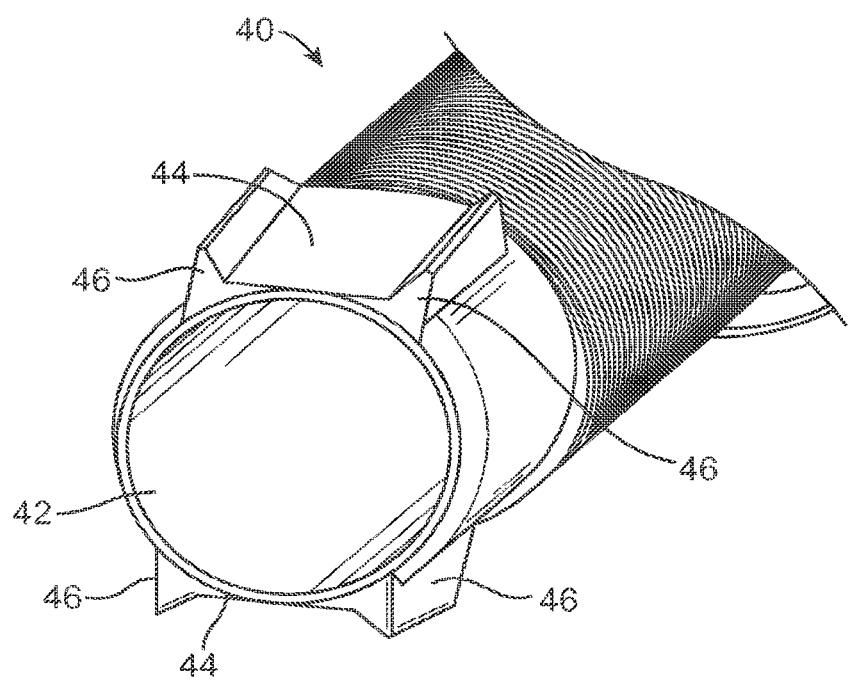
FIG. 8b is a perspective view of a distal end of a cannula according to the present invention.
Figure 9:
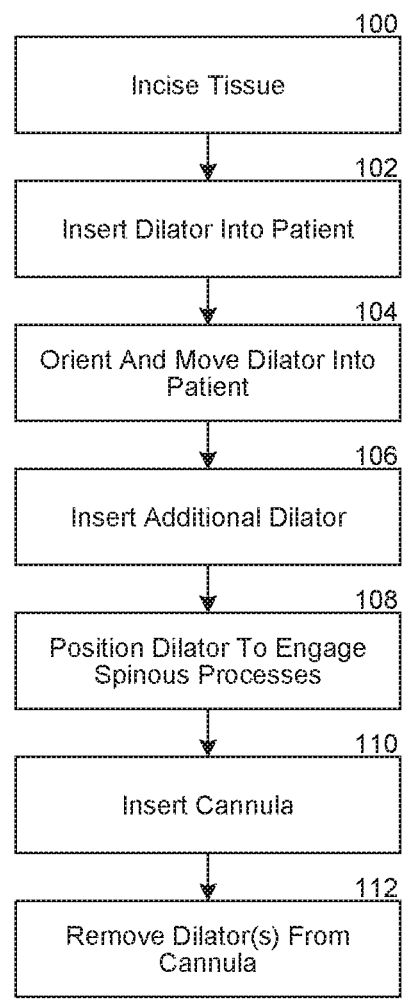
FIG. 9 is a flow chart of a method of treatment according to one embodiment.

An entry point is selected on the patient's skin to obtain access to the targeted surgical site, and an incision of appropriate length (block 100 of FIG. 9) is made through the dermal layers of a patient's body at the entry point. The length and depth of the incision may be larger depending on whether the clinician is using an open, mini-open, or minimally invasive, percutaneous approach. If a guide wire is used, the tip of the guide wire is then positioned within the incision and guided toward the spine using a cannulated T-handled trocar. If a ligament such as the supraspinous or interspinous ligament is to be punctured with a sharp edge other than with the dilator, the sharp edge or scalpel is used to create a small cut in the ligament. One of the first dilators, such as any one of the dilators 10 described above in reference to FIGS. 1-5, is then inserted (over the guidewire if one is used) into the incision (block 102 of FIG. 9) and into the cut in the ligament (if the ligament is pre-cut with a scalpel or other sharp edge). The first dilator is properly oriented (such that diagonal or edges are aligned with ligamentous strands as described above) and further inserted (block 104 of FIG. 9) to spread apart body tissue and/or pierce and/or split and/or cut the ligament. After the first dilator is inserted a second dilator, such as any one of the dilators 10 described above in reference to FIGS. 6-7, is then passed over the proximal end 14 of the first dilator and further passed over the first dilator into the incision to further spread apart tissue and/or split the ligament (block 106 of FIG. 9). Any number of additional dilators, that are preferably cannulated for passing over the one or more previous dilators, are then inserted. At block 108 of FIG. 9, a dilator with a channel 18 is oriented such that one of the adjacent spinous processes is positioned inside the channel 18 and in one variation, the other of the adjacent spinous processes is tracked inside the oppositely located channel 18. Such placement of the dilator with respect to the spinous processes stabilizes the dilator with respect to the spine. Advancement of the dilator relative to the adjacent spinous processes, ramps the adjacent spinous processes first at the tip of the distal portion and then inside the channel 18 if one is employed to distract the adjacent spinous processes. Subsequent dilators placed over the previous dilator may further distract the spinous processes. In one variation, the channels 18 themselves may be flat or further ramped to further distract the adjacent spinous processes. After the desired amount of dilation with dilators is achieved, a cannula 40 of the type shown in FIGS. 8a-8b is passed over the last dilator 10 (block 110 of FIG. 9) such that the dilators 10 are received in the cannula bore 42. The cannula 40 may further include oppositely located channels 44 for receiving the adjacent spinous processes, stabilizing the spinous processes with respect to the dilator and for further distraction of the adjacent spinous processes. The channels 44 are formed by four wings 46 extending outwardly from the surface. At block 112 of FIG. 9, with the cannula 40 in place, the dilators 10 inside the cannula bore 42 are removed leaving an open cannula bore 42 through which surgery can be performed or an implant be inserted.

All publications mentioned anywhere herein are incorporated herein by reference as part of the detailed description of the present invention to disclose and describe the methods and/or materials in connection with which the publications are cited or in connection with the present invention. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope.

We claim:

1. A system comprising:
    a dilator comprising:
       a proximal portion and a distal portion interconnected by an elongated body portion; at least a part of the distal portion has a cross-sectional area decreasing with distance towards a distal end; and
       two oppositely located channels formed in the body portion and extending longitudinally into the distal portion; and
    an instrument configured to be delivered through a subject's supraspinous ligament, the instrument including a tubular body and two oppositely located channels on an outer surface of the tubular body, each of the channels of the instrument defining two sidewalls and a solid base between, and directly connecting, the two sidewalls, and the tubular body having an inner surface defining a passageway configured to receive the dilator and being positioned directly between the passageway and the base of each of the channels of the instrument.

2. The system of claim 1 wherein the instrument is configured to receive the dilator inside the passageway such that the channels of the instrument are aligned with the channels of the dilator.

3. A system comprising:
    a dilator including an elongate body with a first dilator channel and a second dilator channel, wherein the first and second dilator channels extend along a sidewall of the elongate body, wherein the first dilator channel is configured to be positioned to hold a first spinous process of a subject and the second dilator channel is configured to be positioned to hold a second spinous process of the subject; and
    an instrument including a tubular body, a passageway, a first instrument channel, and a second instrument channel, wherein the first instrument channel is configured to receive the first spinous process from the first dilator channel to the first instrument channel, wherein the second instrument channel is configured to receive the second spinous process from the second dilator channel, wherein the tubular body is directly between the passageway and each of the first and second instrument channels, each of the first and second instrument channels defining two sidewalls and a solid base between, and directly connecting, the two sidewalls.

4. The system of claim 3, wherein the dilator and the instrument are configured to be sequentially advanced into the subject to distract the first and second spinous processes.

5. The system of claim 3, wherein the first dilator channel has a solid base and sidewalls spaced apart by the solid base and configured to receive the first spinous process therebetween.

6. The system of claim 3, wherein the dilator has a tapered distal portion extending distally from the first and second dilator channels.

7. The system of claim 3, wherein the instrument is configured to be moved over a proximal end of the elongate body and advanced along the elongate body.

8. The system of claim 3, wherein the first and second instrument channels terminate at locations proximate to a distal portion of the instrument.

9. The system of claim 3, wherein the dilator and the instrument are configured to cooperate to align the first and second dilator channels with the first and second instrument channels, respectively.

10. The system of claim 3, wherein at least a portion of the first instrument channel is sloped and configured to cause distraction of the first and second spinous processes.

11. The system of claim 3, wherein a distal end of the instrument is configured to be positioned directly between the first and second spinous processes, and wherein a distance between the first and second instrument channels increases toward a proximal end of the instrument.

12. The system of claim 3, wherein the dilator is hollow.

13. The system of claim 3, wherein the dilator has a solid cross section.

14. The system of claim 3, wherein the first instrument channel is wider than the first dilator channel.

15. A system comprising:
- a dilator configured to be delivered through a human subject's supraspinous ligament and including
  - a body, and
  - a first dilator channel extending along the body and configured to receive a first spinous process of the human subject; and
- an instrument movable over the dilator and including
  - an instrument body with a dilator-receiving passageway, and
  - a first instrument channel configured to receive the first spinous process while the dilator is positioned in the dilator-receiving passageway, wherein the instrument body is positioned directly between the first instrument channel and the dilator-receiving passageway, the first instrument channel defining two sidewalls and a solid base between, and directly connecting, the two sidewalls.

16. The system of claim 15, wherein the first dilator channel extends longitudinally along the body of the dilator.

17. The system of claim 15, further comprising a second dilator channel that extends longitudinally along the body, and wherein the first and second dilator channels are located on opposite sides of the body.

18. The system of claim 15, further comprising a second instrument channel that extends longitudinally along the instrument body, and wherein the first and second instrument channels are on opposite sides of the instrument body, the second instrument channel defining two sidewalls and a solid base between, and directly connecting, the two sidewalls.

19. The system of claim 15, wherein the first dilator channel and the first instrument channel are configured to be aligned when the dilator is positioned in the dilator-receiving passageway.

20. The system of claim 15, wherein the first dilator channel is narrower than the first instrument channel.

21. The system of claim 15, wherein the first instrument channel has a depth that gradually decreases toward a central region of the instrument.

22. The system of claim 15, wherein the instrument has a proximal end and a distal end, and wherein the first instrument channel has a depth that gradually decreases toward the distal end of the instrument.

23. The system of claim 15, wherein the first instrument channel is sloped and configured to cause distraction of the first and second spinous processes.

24. The system of claim 15, wherein the instrument is a dilator or a cannula.

* * * * *